US008791064B2

(12) United States Patent
Livney

(10) Patent No.: US 8,791,064 B2
(45) Date of Patent: Jul. 29, 2014

(54) BETA-LACTOGLOBULIN-POLYSACCHARIDE NANOPARTICLES FOR HYDROPHOBIC BIOACTIVE COMPOUNDS

(75) Inventor: Yoav D. Livney, Misgav (IL)

(73) Assignee: Technion Research and Development Foundation Ltd., Haifa (IL)

( * ) Notice: Subject to any disclaimer, the term of this patent is extended or adjusted under 35 U.S.C. 154(b) by 524 days.

(21) Appl. No.: 12/989,384

(22) PCT Filed: Apr. 26, 2009

(86) PCT No.: PCT/IL2009/000446
§ 371 (c)(1),
(2), (4) Date: Nov. 3, 2010

(87) PCT Pub. No.: WO2009/130704
PCT Pub. Date: Oct. 29, 2009

(65) Prior Publication Data
US 2011/0038942 A1 Feb. 17, 2011

Related U.S. Application Data

(60) Provisional application No. 61/047,440, filed on Apr. 24, 2008.

(51) Int. Cl.
C07K 14/00 (2006.01)
A61K 9/16 (2006.01)
A61K 38/00 (2006.01)

(52) U.S. Cl.
USPC .............. 514/2; 424/484; 424/499; 977/773; 977/906

(58) Field of Classification Search
None
See application file for complete search history.

(56) References Cited

U.S. PATENT DOCUMENTS

| | | | |
|---|---|---|---|
| 3,958,581 | A | 5/1976 | Abegg |
| 3,962,418 | A | 6/1976 | Birkofer |
| 6,190,591 | B1 | 2/2001 | Van Lengerich |
| 6,290,974 | B1 | 9/2001 | Swaisgood |
| 6,428,814 | B1 | 8/2002 | Bosch |
| 6,528,497 | B1 | 3/2003 | Basten |
| 2003/0185960 | A1 | 10/2003 | Augustin |
| 2006/0134282 | A1 | 6/2006 | Mellema |
| 2007/0085058 | A1 | 4/2007 | Mora-Gutierrez |
| 2007/0231453 | A1 | 10/2007 | Bovetto |
| 2009/0035437 | A1 | 2/2009 | Bovetto |
| 2012/0093933 | A1 | 4/2012 | Livney |

OTHER PUBLICATIONS

Ron, N., "Beta Lactoglobulin as a Nano-Capsular Vehicle for Hydrophobic Nutraceuticals", M.Sc. Thesis, www.graduate.technion.ac.il/theses/Advisors.asp?Key=20867 (Abstract only).*
Brownlow, Sharon et al., (1997) Bovine beta-lactoglobulin at 1.8 A resolution—still an enigmatic lipocalin. Structure 5(4):481-495.
Chen, Lingyun and Subirade, Muriel (2005) Chitosan/beta-lactoglobulin core-shell nanoparticles as nutraceutical carriers. Biomaterials 26(30):6041-6053.
Chen, Lingyun et al., (2006) Food protein-based materials as nutraceutical delivery systems. Trends Food Sci Technol 17(5):272-283.
Christiaens, Bart et al., (2002) Tryptophan fluorescence study of the interaction of penetratin peptides with model membranes. Eur J Biochem 269(12):2918-2926.
Cogan, Uri et al., (1976) Binding affinities of retinol and related compounds to retinol binding proteins. Eur J Biochem 65(1):71-78.
De Kruif, Cornelus G. et al., (2004) Complex coacervation of proteins and anionic polysaccharides. Curr Opin Colloid Interface Sci 9(5):340-349.
Delgado, A. V. et al., (2005) Measurement and Interpretation of Electrokinetic Phenomena (IUPAC Technical Report). Pure Appl Chem 77(10):1753-1805.
Garti, Nissim et al., (2004) Transitions and loci of solubilization of nutraceuticals in U-type nonionic microemulsions studied by self-diffusion NMR. Phys Chem Chem Phys 6(11):2968-2976.
Gosal, Walraj S. et al., (2002) Novel Amyloid Fibrillar Networks Derived from a Globular Protein: β-Lactoglobulin. Langmuir 18(19):7174-7181.
Hong, Youn-Ho and McClements, David Julian (2007) Formation of hydrogel particles by thermal treatment of beta-lactoglobulin-chitosan complexes. J Agric Food Chem 55(14):5653-5660.
Jameson, Geoffrey B. et al., (2002) Flexibility, functionality and hydrophobicity of bovine β-lactoglobulin. Int Dairy J 12(4):319-329.
Jones, Owen G. and McClements, D. Julian (2008) Stability of biopolymer particles formed by heat treatment of beta lactoglobulin/beet pectin electrostatic complexes. Food Biophysics 3(2):191-197.
Kontopidis, G. et al., (2004) Invited review: beta-lactoglobulin: binding properties, structure and function. J Dairy Sci 87(4):785-796.
Liang, Li et al., (2008) Interaction of beta-lactoglobulin with resveratrol and its biological implications. Biomacromolecules 9(1):50-56 Epub Dec. 8, 2007.
Livney, Yoav G. (2003) Steric effects governing disulfide bond interchange during thermal aggregation in solutions of beta-lactoglobulin B and alpha-lactalbumin. J Agric Food Chem 51(27):8098-8106.
Livney, Yoav D. Complexes and conjugates of biopolymers for delivery of bioactive ingredients via food. in: Delivery and controlled release of Bioactives in foods and nutraceuticals, N. Garti (Ed.), Woodhead Publishing Ltd. Abington, Cambridge, England 2008. pp. 234-250.
Namani, Trishool et al., (2007) Vesicles from docosahexaenoic acid. Colloids and Surfaces B: Biointerfaces 54 (1):118-123.
Okada, Masahiko et al., (1983) Chemical Synthesis of Polysaccharides III. A Synthetic Polysaccharide Having One Hydroxyl Group in Its Repeating Unit, 3,4-Dideoxy-(1→)-α-DL-threo-hexopyranan. Polymer Journal 15 (11):821-826.

(Continued)

Primary Examiner — Anand Desai
(74) Attorney, Agent, or Firm — Rodney J. Fuller; Booth Udall Fuller, PLC

(57) ABSTRACT

The present invention provides colloidally stable dispersions of nanoparticles comprising beta-lactoglobulin and a polysaccharide which are transparent when diluted in aqueous media. In particular these colloidally stable dispersions of nanoparticles are useful as delivery vehicles of hydrophobic nutraceuticals and fat-soluble vitamins, for enrichment of food products, especially of transparent beverages and other non-fat or low fat foods and drinks. The present invention further provides methods for the preparation of said colloidally stable dispersions.

28 Claims, 10 Drawing Sheets

(56) References Cited

OTHER PUBLICATIONS

Renard, D. et al., (2002) Biopolymeric colloidal carriers for encapsulation or controlled release applications. Int J Pharm 242(1-2):163-166.

Riihimaki, L. H. et al., (2008) Binding of phenolic compounds and their derivatives to bovine and reindeer beta-lactoglobulin. J Agric Food Chem 56(17):7721-7729.

Ron, N. "Beta lactoglobulin as a nano-capsular vehicle for hydrophobic nutraceuticals" [online] 2007 The Technion, Israel Institute of Technology, Haifa, Israel. Retrieved from the internet: URL:http://www.graduate.technion.ac.il/theses/advisors.asp?key=20867> Retrieved on Aug. 6, 2008 abstract.

Ron, N. "Beta lactoglobulin as a nano-capsular vehicle for hydrophobic nutraceuticals" Thesis Apr. 1, 2007 pp. 1-45.

Schmitt, Christophe et al., (1998) Structure and technofunctional properties of protein-polysaccharide complexes: a review. Critical Reviews in Food Science and Nutrition 38(8):689-753.

Semo, Efrat et al., (2007) Casein micelle as a natural nano-capsular vehicle for nutraceuticals. Food Hydrocolloids 21 (5-6):936-942.

Subirade, Muriel et al., (2003) Whey protein-derived biomaterials and their use as bioencapsulation and delivery systems. Chem Ind 57(12):617-621.

Wang, Qiwu et al., (1997) Binding of Retinoids to β-Lactoglobulin Isolated by Bioselective Adsorption. J Dairy Sci 80 (6):1047-1053.

Wang, Qiwu et al., (1997) Binding of Vitamin D and Cholesterol to β-Lactoglobulin. J Dairy Sci 80(6):1054-1059.

Yaghmur, A. et al., (2004) Structural characterization of five-component food grade oil-in-water nonionic microemulsions. Phys Chem Chem Phys 6(7):1524-1533.

Zimet, P., and Livney, Y. D. (2009) Beta-lactoglobulin and its nanocomplexes with pectin as vehicles for [omega]-3 polyunsaturated fatty acids. Food Hydrocolloids 23(4):1120-1126.

ISR of PCT/IL2009/000446 mailed Sep. 23, 2009.

Boger, Rainer H., "The pharmacodynamics of L-Arginie", The Journal of Nutrition, 137, 2007, 1650S-1655S.

Ru, Q. et al. "Encapsulation of epigallocatechin-3-gallate (EGCG) using oil-in-water (0/W) submicrometer emulsions stabilized by 1-carrageenan and l3-lactoglobulin", J Agric Food Chem. Oct. 13, 2010; 58(19):1 0373-0381.

Non-final Rejection of U.S. Appl. No. 131275,223, dated Nov. 16, 2012.

Pan et al., (2007) Simultaneous nanoparticle formation and encapsulation driven by hydrophobic interaction of casein-graft-dextran and beta-carotene. J Colloid Interface Sci 315(2): 456-63.

Zhang et al., (2009) Macromolecular conjugate based particulates: Preparation, characterization and evaluation of controlled release properties. European Polymer Journal, 45(7): 1960-1969.

\* cited by examiner

BETA-LACTOGLOBULIN-POLYSACCHARIDE NANOPARTICLES FOR HYDROPHOBIC BIOACTIVE COMPOUNDS

RELATED APPLICATION DATA

This application is the U.S. national stage of PCT/IL2009/000446, filed Apr. 26, 2009, which claims the benefit of U.S. Provisional Application No. 61/047,440, filed Apr. 24, 2008, the contents of each of which are herein incorporated by reference for all purposes.

FIELD OF INVENTION

The present invention relates to β-lactoglobulin-polysaccharide nanoparticles useful for encapsulating, stabilizing and protecting a variety of bioactive compounds and methods of making the nanoparticles. In particular, the present invention relates to colloidally stable dispersions of β-lactoglobulin-polysaccharide nanoparticles encapsulating hydrophobic bioactive compounds which are transparent in aqueous media and are useful as food additives.

BACKGROUND OF THE INVENTION

The enrichment of foods with hydrophobic biologically active compounds, including hydrophobic nutraceuticals and fat-soluble vitamins is a promising strategy for promoting health of global populations. However, the desire for reduction of fat content in a healthy diet creates a difficulty in providing the required amounts of essential hydrophobic biologically active compounds, including fat-soluble vitamins and hydrophobic nutraceuticals. Moreover, many hydrophobic biologically active compounds degrade easily during processing, shelf life and digestion. The need for enrichment of food products with hydrophobic biologically active compounds motivates the development of novel technologies for solubilizing, stabilizing and protecting such hydrophobic biologically active compounds using natural food components.

Clear drinks, which are consumed in large quantities, pose a particularly important challenge because of the difficulty of incorporating oil-soluble materials in a clear and stable aqueous dispersion. The ideal vehicle for the task should be nano-sized to maintain transparency and composed of only natural, generally regarded as safe and inexpensive food components, capable of solubilizing and protecting hydrophobic biologically active compounds in aqueous media while retaining sensory qualities, and promoting bioavailability of hydrophobic biologically active compounds. Very few solutions for these challenging requirements have been suggested and none has all the desired attributes. Micro- or nanoemulsions may have excellent transparency (Garti et al., (2004) *Physical Chemistry and Chemical Physics* 6, 2968; Yaghmur et al., (2004) *Physical Chemistry and Chemical Physics* 6, 1524), but generally require the presence of a high proportion of synthetic emulsifiers that are not desirable ingredients.

Milk protein-based nanoparticles offer the potential for nanoencapsulation of nutraceuticals (Chen et al., (2006) *Trends in Food Sci. and Technology* 17, 272; Semo et al., (2007) *Food Hydrocolloids* 21,936; Subirade et al., (2003) *Hemijska Industrija* 57, 617), as many of the milk proteins have naturally evolved to deliver nutrients from mother to neonate. β-lactoglobulin was suggested as a suitable vehicle for delivery of hydrophobic biologically active compounds, as it had been shown to bind a variety of lipophilic micronutrients (Wang et al., (1997a) *J. Dairy Sci.* 80:1047; Wang et al., (1997b) *J. Dairy Sci.* 80:1054; Zimet and Livney (2009) *Food Hydrocolloids* 23:1120). It is the major whey protein of ruminant species, (2-3 grams per liter in cow's milk, 18.4 kDa) (Hambling et al., (1992) In P. F. Fox (Ed.), Advanced Dairy Chemistry-1: Proteins p. 141 London & New York: Elsevier Applied Science; Jameson et al., (2002) *Int. Dairy J.* 12, 319), and its globular structure comprises an 8-stranded antiparallel β-barrel with a 3-turn α-helix on the outer surface (Brownlow et al., (1997) *Structure* 5, 481). The solvent accessible conical β-barrel, or calyx, forms the main ligand binding site, although evidence suggests that there is a second ligand binding site in a crevice near the α-helix on the external surface of the β-barrel (Kontopidis et al., (2004) *Int. Dairy J.* 12, 319). Native β-lactoglobulin is stable in acid conditions, and quite resistant to digestion by gastric proteinases (Wang et al., (1997a) *J. Dairy Sci.* 80, 1047; Wang et al., (1997b) *J. Dairy Sci.* 80, 1054). However, the main shortcoming of β-lactoglobulin as a nanovehicle for hydrophobic biologically active compounds is that β-lactoglobulin binding sites are solvent-accessible, and thus the ligand is only partly protected from the environment.

U.S. Pat. No. 6,290,974 teaches a food composition comprising a food additive comprising a preformed complex comprising β-lactoglobulin and a lipophilic nutrient selected from the group consisting of vitamin A, vitamin D, vitamin E, vitamin $K_1$, cholesterol, and conjugated linoleic acid. In that disclosure the lipophilic nutrient is bound to β-lactoglobulin via one or more amino acid residues. Nowhere in U.S. Pat. No. 6,290,974 is it disclosed, taught or suggested that polysaccharides can be added to β-lactoglobulin-lipophilic nutrient complexes to form clear colloidally stable dispersions of nanoparticles for enhanced protection of the lipophilic nutrient.

Attractive biopolymer interactions mainly occur between positively charged proteins (when the pH<pI) and anionic polysaccharides or negatively charged proteins (when the pH>pI) and cationic polysaccharides. These interactions result in complex formation, and depending on pH, ionic strength and molar ratio of the two biopolymers, may lead to formation of either soluble complexes or to complex coacervation, i.e. associative phase separation. Soluble complexes may be obtained when opposite charges carried by the two macro-ions within a complex are not equal in number. The resulting net charge allows the complex solubilization thanks to the high entropy of the low molecular weight counter ions, as well as to the repulsion between the similarly charged complexes. However, when the opposite charges carried by the two biopolymers neutralize each other, the complexes become insoluble, resulting in coacervation and precipitation (de Kruif et al., (2004) *Curr. Opin. Colloid & Interface Sci.* 9, 340; Livney, (2007) in N. Garti (Ed.), Delivery and controlled release of bioactives in foods and nutraceuticals. Cambridge, England: Woodhead Publishing Ltd; Schmitt et al., (1998) *Critical Reviews in Food Science and Nutrition* 38, 689).

Core-shell nanoparticles of chitosan coated with β-lactoglobulin were proposed for delivery of nutraceuticals (Chen and Subirade, (2005) *Biomaterials* 26, 6041). The particles formed were about 100 nm in size, and were designed to encapsulate negatively charged nutraceuticals, as the cationic chitosan served as the core while β-lactoglobulin was used as the coating material. These nanoparticles were not made of only natural ingredients and preferably included tripolyphosphate as a cross-linker for nano gel-particle formation. In addition, nowhere is it taught or suggested in this reference, that the core-shell β-lactoglobulin-chitosan nanoparticles formed were clear in suspension or that they could be used for hydrophobic nutraceuticals.

Vitamin D is a fat-soluble vitamin of great importance in calcium and phosphate metabolism, i.e. in facilitation of calcium absorption in the intestine, transporting calcium and phosphate to the bones and re-absorption of calcium and phosphate in the kidneys. Vitamin D also takes part in the formation of osteoblasts, in fetal development and in the normal function of the nerve system, the pancreas and the immune system (Eintenmiller, R. R. and Landen, W. O., (1999) In Vitamin analysis for the health and food science Lawson, D. E. M. (Ed.) CRC Press: Boca Raton p. 77). However, because vitamin D is fat-soluble it is practically absent in low-fat and non-fat dairy products, important sources for calcium and phosphate, which are consumed in large quantities, particularly in modern societies. Additionally, solubility of vitamin D and other fat-soluble vitamins in other low-fat and non-fat food products is very low.

Vitamin D has over 40 known metabolites, one of which is vitamin D2. Vitamin D2 originates from plants. It is found in nature in limited amounts, but can be synthesized readily. The vitamin structure contains double bonds that are sensitive to oxidation. Light, air and high temperature induce vitamin isomerization or degradation into inactive products (Eintenmiller, R. R. and Landen, W. O., (1999) In Vitamin analysis for the health and food science CRC Press: Boca Raton p. 77; Bell, A. B. (2005) In Vitamin D Lawson, D. E. M. (Ed.) London, Academic Press p. 1).

Omega-3 polyunsaturated fatty acids are gaining increasing recognition as important nutraceutical lipids, playing significant roles in protecting against cardiovascular diseases, cancer, and inflammation. Moreover, many studies show that consumption of omega-3 polyunsaturated fatty acids, especially docosahexaenoic acid (DHA), positively influences brain development, learning and memory, visual function, and exerts remedial effects on dementia and mental disorders. Not only is DHA poorly soluble in aqueous solutions but because DHA is highly unsaturated, it is also very sensitive to oxidative degradation, leading to off-flavors and odors. Factors affecting oxidation rates include fatty acid composition, storage conditions and physical state.

There remains an unmet need for compositions and methods useful in enriching low-fat and non-fat food products with hydrophobic biologically active compounds. Particularly, there is a need in the art for compositions and methods of providing hydrophobic biologically active compounds as additives with enhanced stability and without compromising bioavailability or sensorial characteristics of foods, such as transparency and flavor.

SUMMARY OF THE INVENTION

The present invention provides compositions and methods for the formation of stable colloidal dispersions of nanoparticles useful as carriers for biologically active compounds. The nanoparticles according to the invention are small enough so as not to compromise the transparency of clear beverages and the appearance of foods into which they are incorporated. Thus, the present invention provides compositions and methods for fowling transparent, colloidally stable dispersions of β-lactoglobulin-polysaccharide nanoparticles encapsulating biologically active compounds for the enrichment of and the delivery via food products of the encapsulated biologically active compounds. The nanoparticles disclosed in the present invention further stabilize and protect the biologically active compounds encapsulated therein against degradation by oxidation and other chemical and enzymatic reactions during production and shelf life. Advantageously, the β-lactoglobulin-polysaccharide nanoparticles disclosed in the present invention preferably comprise only natural, generally regarded as safe and non-toxic components.

Thus, the present invention provides transparent, stable colloidal dispersions of β-lactoglobulin/polysaccharide nanoparticles suitable as carriers of bioactive compounds, preferably oil-soluble vitamins, nutraceuticals and pharmaceuticals, useful for addition of bioactive compounds with improved stability, into transparent beverages and other foods and drinks, for example, non-fat or low-fat beverages, acidic non-fat or low-fat beverages and milk products.

The present invention is based in part on the finding that charged nanoparticles are formed between β-lactoglobulin and an excess of polysaccharide under conditions at which the β-lactoglobulin and the polysaccharide are oppositely charged. Particularly, it is now shown for the first time that these charged nanoparticles form, upon dilution, transparent solutions, with a very good colloidal stability and an average particle size of ~100 nm.

The present invention is further based on the finding that hydrophobic nutraceuticals, which spontaneously bind β-lactoglobulin, can be encapsulated within the β-lactoglobulin/polysaccharide nanoparticles. Unexpectedly, the β-lactoglobulin-polysaccharide nanoparticles retained their small particle size and showed colloidal stability and exceedingly low turbidity even in the presence of the encapsulated nutraceuticals. Moreover, it was shown that such encapsulation provides better protection of the nutraceuticals against degradation or oxidation, than by β-lactoglobulin as a sole entrapping vehicle. The compositions of isolated β-lactoglobulin with excess polysaccharide further comprising vitamins or nutraceuticals are exemplified herein below by docosahexanoic acid (DHA) and vitamin D, as particular embodiments.

According to one aspect, the present invention provides a stable colloidal dispersion of nanoparticles comprising isolated β-lactoglobulin and a polysaccharide. Preferably the stable colloidal dispersion of nanoparticles is transparent in an aqueous medium. According to some embodiments the isolated β-lactoglobulin according to the present invention is substantially free of other protein, and is at least 80%, 85%, 90% or even 95% or more pure. Within the scope of the present invention are nanoparticles comprising more than one polysaccharide. According to certain embodiments, the polysaccharide is an anionic polysaccharide. According to another embodiment, the polysaccharide is a cationic polysaccharide.

The term 'anionic polysaccharide' as used herein refers to a polysaccharide which is negatively charged, particularly at a pH lower than the pI of β-lactoglobulin, the pI of β-lactoglobulin being 5.1.

The term 'cationic polysaccharide' as used herein refers to a polysaccharide which is positively charged, particularly at a pH higher than the pI of β-lactoglobulin.

According to certain embodiments of the present invention the anionic polysaccharides are selected from the group consisting of pectin, alginic acid, xanthan gum, hyaluronic acid, chondroitin sulfate, gum arabic, gum karaya, gum tragacanth, carrageenan, agaropectin and aloe pectin. According to other embodiments the anionic polysaccharides of the present invention include any other polysaccharide which is negatively charged at a pH lower than the pI of β-lactoglobulin. According to some preferred embodiments the anionic polysaccharide is a pectin. According to some embodiments the pectin is selected from high methoxy and low methoxy pectin. According to some preferred embodiments of the present invention the pectin is a low methoxy pectin.

The term 'low methoxy pectin' as used herein refers to a pectin molecule in which not more than 50% of the carboxylate groups are esterified; preferably less than 40% of the carboxylate groups are esterified; preferably less than 35% of the carboxylate groups are esterified; more preferably less than 30% of the carboxylate groups are esterified; even more preferably less than 25% of the carboxylate groups are esterified.

According to certain embodiments of the present invention the cationic polysaccharide are selected from the group consisting of diethylaminoethyl dextran, guar gum derivatives (such as guar hydroxypropyltrimonium chloride), quaternary nitrogen-containing cellulose ethers, cationic cellulose (such as Polyquaternium 10 and Polyquaternium 24) and chitosan. According to some other embodiments the cationic polysaccharides include any polysaccharide carrying an amino group or an imine group. However, it should be noted that according to some embodiments, chitosan nanoparticles are excluded from the present invention, such that any of the embodiments described herein may optionally have the proviso that the polysaccharide does not comprise chitosan. Optionally and more preferably, for those embodiments which encompass chitosan, the nanoparticles are limited to the particles i) excluding additional polyionic gelling, or cross-linking agents such as sodium tripolyphosphate and ii) not having a core-shell structure in which the core chitosan polysaccharide is coated by β-lactoglobulin molecule.

According to some embodiments the amount of polysaccharide in the colloidal nanoparticles of the invention is equal to or higher than the amount of β-lactoglobulin. According to some other embodiments the weight ratio between the β-lactoglobulin and the polysaccharide is between about 1:1 and about 1:10. Preferably the weight ratio between β-lactoglobulin and the polysaccharide is between about 1:1 and about 1:5. More preferably the weight ratio between β-lactoglobulin and the polysaccharide is between about 1:1 and about 1:3. According to certain embodiments preferably the ratio between β-lactoglobulin and the polysaccharide is between about 1:1 and about 1:2.

According to some embodiments the average molecular weight of the polysaccharide is below 1,000,000 Da. According to some other embodiments the average molecular weight of the polysaccharide is below 100,000 Da.; preferably, the average molecular weight of the polysaccharide is below 50,000 Da.; more preferably, the average molecular weight of the polysaccharide is 20,000 Da and below.

According to some embodiments the dispersion of nanoparticles according to the present invention comprises up to about 0.5 wt % of β-lactoglobulin. According to some other embodiments the dispersion of nanoparticles comprises up to about 0.2 wt % of β-lactoglobulin. According to some other embodiments the dispersion of nanoparticles comprises up to about 0.1% β-lactoglobulin. According to some preferred embodiments the dispersion of nanoparticles comprises about 0.05 wt % of β-lactoglobulin.

The present invention provides colloidal dispersions of nanoparticles, the dispersion being transparent in an aqueous medium. Without wishing to be bound by theory, the transparency is directly related to the size of the nanoparticles of the invention, as well as to their concentration. According to some embodiments the diameter of the nanoparticles of the invention is between about 20 and about 400 nm, more typically the nanoparticles of the present invention have a diameter below about 300 nm, preferably below about 200 nm, more preferably below about 150 nm, even more preferably the diameter of nanoparticles of the invention is of about 100 nm or below.

The dispersion of nanoparticles of the present invention is stable and transparent at a wide range of pHs from about 3.0 to about 7.0. Without wishing to be bound by theory or mechanism of action, the interaction between the β-lactoglobulin and the polysaccharide is mainly controlled by electrostatic forces. As such and according to several embodiment of the present invention, the dispersion of nanoparticles comprising anionic polysaccharides will preferably be dispersed in an aqueous solution having a pH below the pI of β-lactoglobulin. Under such acidic conditions the β-lactoglobulin is positively charged, whereas the anionic polysaccharide is negatively charged. According to some other embodiment the dispersion of nanoparticles comprising anionic polysaccharides and β-lactoglobulin will be preferably dispersed in an aqueous solution having a pH between about 3.0 and about 5.0. Preferably the dispersion of nanoparticles comprising anionic polysaccharides and β-lactoglobulin will be dispersed in an aqueous solution having a pH between about 3.5 and about 4.5. According to some other embodiments, the dispersion of nanoparticles comprising cationic polysaccharides will be preferably dispersed in an aqueous solution having a pH above the pI of β-lactoglobulin. Under neutral pH the β-lactoglobulin is negatively charged, whereas the cationic polysaccharide is positively charged. According to some other embodiment the dispersion of nanoparticles comprising cationic polysaccharides will be preferably dispersed in an aqueous solution having a pH between about 5.0 and about 8.0. Preferably the dispersion of nanoparticles comprising anionic polysaccharides will be dispersed in an aqueous solution having a pH between about 5.5 and about 7.0. Most preferably the dispersion of nanoparticles will be dispersed in an aqueous solution having a pH between about 5.5 and about 6.5.

Without wishing to be bound by theory or mechanism of action, upon interaction of the β-lactoglobulin with an excess of polysaccharide, it is believed that the nanoparticles of the invention are generally coated with the excess polysaccharide. Accordingly, the polysaccharide having been selected to be cationic or anionic, forms charged nanoparticles in which local charged loci on the surface of the β-lactoglobulin molecules interact with an oppositely charged functional groups on the polysaccharide. In the presence of an excess of polysaccharide, the β-lactoglobulin-polysaccharide nanoparticles are presumably coated by the excess polysaccharide, thereby creating a structure in which β-lactoglobulin is found in the inner part of a nanoparticle which is further coated by the polysaccharide. Nanoparticles of the invention may be spherical or have other shapes.

The dispersion of nanoparticles of the present invention is highly stable. According to some embodiments of the present invention the dispersion of nanoparticles is transparent in aqueous media and transparency is maintained for several months. According to certain embodiments the nanoparticles remain dispersed in solution without sedimenting out for at least 1 month at ambient temperature; alternatively, for at least 2 months at ambient temperature; alternatively, for at least 3 months at ambient temperature; alternatively, for at least 4 months at ambient temperature; alternatively, for at least 5 months at ambient temperature; alternatively, for at least 6 months at ambient temperature; alternatively, for more than 6 months at ambient temperature. It is to be understood that the nanoparticles remain dispersed in solution without sedimenting out for longer periods of time under cold storage, e.g., 2-8° C.

Turbidity is one of the parameters used to estimate the stability of the colloidal dispersion of nanoparticles in aqueous media according to the present invention. According to some embodiments, the turbidity of an aqueous solution (being non-fat or low-fat) comprising the colloidal dispersion of nanoparticles of the present invention is less than 0.25 for at least 1 month; alternatively, less than 0.2 for at least one month; alternatively, less than 0.15 for at least one month; alternatively, of about 0.1 for at least one month.

According to another aspect, the present invention provides a stable colloidal dispersion of nanoparticles comprising isolated β-lactoglobulin, a polysaccharide and at least one bioactive compound. According to a preferred embodiment the dispersion of nanoparticles comprising at least one bioactive compound is transparent in an aqueous medium. According to some embodiments the polysaccharide is selected from the group consisting of anionic polysaccharide and cationic polysaccharide. According to certain preferred embodiments the polysaccharide is an anionic polysaccharide. According to some embodiments the polysaccharide is other than chitosan.

According to embodiments of the present invention the bioactive compound is selected from the group consisting of a vitamin, a nutracetical and a pharmaceutical. According to certain embodiments, the biologically active compound is hydrophobic. According to certain embodiments, the biologically active compound is encapsulated within the β-lactoglobulin-polysaccharide nanoparticle. According to certain embodiments the bioactive compound is bound to the β-lactoglobulin. Without wishing to be bound by theory or mechanism of action, the bioactive compound is bound to the hydrophobic core of β-lactoglobulin preferably by hydrophobic interactions.

According to some embodiments the molar ratio between the β-lactoglobulin and the bioactive compound is of about 3:1 to about 1:10. According to other embodiments the ratio between the β-lactoglobulin and the bioactive compound is of about 1:1 to about 1:5. According to some preferred embodiments the ratio between the β-lactoglobulin and the bioactive compound is from about 1:1 to about 1:3.

According to certain embodiments, the vitamin is a fat-soluble vitamin. According to another embodiment, the fat-soluble vitamin is selected from the group consisting of vitamin D, vitamin E, vitamin A and vitamin K. According to an exemplary embodiment, the fat-soluble vitamin is vitamin D2. According to another exemplary embodiment, the nanoparticles comprise pectin as the polysaccharide and vitamin D2. According to yet another exemplary embodiment, the nanoparticles comprise chitosan as the polysaccharide and vitamin D2. According to other embodiments the molar ratio of β-lactoglobulin and vitamin D2 is between 3:1 and 1:3, most typically 1:1.

According to some embodiments, the nutraceutical is selected from the group consisting of an essential fatty acid a phytoestrogen and an antioxidant. According to one embodiment the essential fatty acid is selected from the group consisting of an omega-3 fatty acid and a conjugated linoleic acid. According to another embodiment the omega-3 fatty acid is selected from the group consisting of docosahexaenoic acid (DHA), eicosapentaenoic acid, α-linolenic acid, stearidonic acid eicosatrienoic acid, eicosatetraenoic acid and docosapentaenoic acid. According to one preferred embodiment the omega-3 fatty acid is DHA. According to one exemplary embodiment the nanoparticles comprise pectin as the polysaccharide and DHA. According to other embodiments the molar ratio of β-lactoglobulin and DHA is between 1:1 and 1:3, most typically between 1:1 and 1:2.

According to some embodiments, the nutraceutical is selected from phytoestrogens including phytosterols (e.g. β-sitosterol, campesterol, stigmasterol etc.), isoflavones (genistein, daidzein), stilbenoids (e.g. trans-resveratrol), lignans (e.g. matairesinol) and coumestans (e.g. coumestrol).

The nanoparticles of the present invention effectively confer protection to the encapsulated bioactive compound against degradation or oxidation. According to some embodiments less than 25% of the encapsulated bioactive compound is degraded or oxidized within 100 hours at 40° C.; alternatively less than 20% of the encapsulated bioactive compound is degraded or oxidized within 100 hours at 40° C.; alternatively less than 15% of the encapsulated bioactive compound is degraded or oxidized within 100 hours at 40° C.; alternatively, less than 10% of the encapsulated bioactive compound is degraded or oxidized within 100 hours at 40° C.

According to another aspect, the present invention provides a food composition or a beverage comprising the stable colloidal dispersion of nanoparticles comprising at least one bioactive compound according to embodiments of the invention and a low-fat or non-fat food or beverage. According to one embodiment the food composition comprises a vitamin as the bioactive compound. According to one preferred embodiment the food composition comprises vitamin D2 as the bioactive compound. According to another embodiment the food composition comprises an essential fatty acid as the bioactive compound. According to another embodiment the food composition comprises an omega-3 fatty acid as the bioactive compound. According to a preferred embodiment, the food composition comprises DHA as the bioactive compound.

According to the present invention the compositions of the invention may further comprise excipients as are suitable for food products. Non-limiting examples of such agents include flavorants, fragrances preservatives and coloring agents.

According to another aspect, the present invention provides a pharmaceutical composition comprising a dispersion of nanoparticles according to embodiments of the present invention.

According to another aspect, the present invention provides a method for the preparation of a stable colloidal dispersion of nanoparticles comprising β-lactoglobulin and a polysaccharide which is transparent in aqueous medium, the method comprising the steps of: (a) mixing a first aqueous solution comprising β-lactoglobulin with a second aqueous solution comprising a polysaccharide to obtain a dispersion of nanoparticles, wherein the weight ratio between the β-lactoglobulin and the polysaccharide is between about 1:1 and 1:5, preferably between about 1:1 and 1:3, and most preferably between 1:1 and 1:2 and (b) adjusting the pH of the dispersion of step (a) to a pH in the range of about 3.0 to about 7.0.

According to one embodiment the β-lactoglobulin concentration after mixing is lower than 0.5%, preferably lower than 0.2%, most preferably about 0.05%. According to one embodiment, the polysaccharide solution is added dropwise into the β-lactoglobulin solution while the solution is vigorously stirred. It is to make clear that as long as the β-lactoglobulin amount is greater than the amount of the polysaccharide, an unstable opalescent dispersion is obtained, which tends to coacervate and precipitate. However, as the amount of polysaccharide in the solution increases to being at least equal and preferably exceeding the β-lactoglobulin amount, the dispersion obtained becomes transparent with no observed precipitation.

According to one embodiment the pH of the solution comprising the nanoparticles of the invention is adjusted according to step (b) to a pH between 3.0 and 5.0 and preferably to a pH between 3.5 and 4.5 when the polysaccharide is an anionic polysaccharide. According to another embodiment the pH of the solution is adjusted according to step (b) to a pH between 5.0 and 7.0 and preferably to a pH between 5.5 and 6.5 when the polysaccharide is a cationic polysaccharide. According to another embodiment the colloidal dispersion of nanoparticles obtained in step (b) is further filtered to remove any particles with a diameter larger than about 200 nm; alternatively the colloidal dispersion of nanoparticles obtained in step (b) is further centrifuged.

According to another aspect, the present invention provides a method for the preparation of stable colloidal dispersion of nanoparticles comprising β-lactoglobulin, a polysaccharide and at least one bioactive compound, the method comprising the steps of:

(a) mixing a water-miscible organic solution (e.g. ethanolic solution) comprising at least one hydrophobic bioactive compound, with an aqueous solution of β-lactoglobulin to obtain a molar ratio between β-lactoglobulin and the bioactive compound in the range of about 3:1 to about 1:10, typically a molar ratio in the range of 1:1 and 1:5 and more typically between 1:1 and 1:3;

(b) adding an aqueous solution of a polysaccharide to the solution prepared in step (a) while mixing, to obtain a dispersion of nanoparticles, wherein the weight ratio between the β-lactoglobulin and the polysaccharide is between about 1:1 and 1:5, preferably between about 1:1 and 1:3, and most preferably between 1:1 and 1:2;

(c) adjusting the pH of the dispersion of step (b) to a pH in the range of about 3.0 to about 7.0.

According to one embodiment the bioactive compound is hydrophobic. According to another embodiment the nanoparticles of the invention are prepared by first forming a complex between the β-lactoglobulin and the bioactive compound. The nanoparticles of the present invention can be prepared by first mixing the bioactive compound dissolved in an organic solvent or cosolvent, such as ethanol, with the aqueous β-lactoglobulin solution at acidic or neutral pH during vigorous stirring. Typically the amount of ethanol added to the aqueous solution is between 0.05 and about 20%. More typically, between about 0.1 and about 10%. Even more typically, between 0.1 and about 8%. Yet even more typically, between 0.1 and 5%. Within the scope of the present invention are also methods according to which the bioactive compound is added to the pre made dispersion of nanoparticles comprising β-lactoglobulin and a polysaccharide.

It is to be explicitly understood that within the scope of the present invention, the compositions may comprise more than one bioactive compound. For example, each of the bioactive compounds may be dissolved in an organic, water miscible solvent (e.g. ethanol, dimethyl sulfoxide (DMSO), and then combined with an aqueous solution of β-lactoglobulin having an acidic or neutral pH. The bioactive compounds may be dissolved in the same organic solvent at a desired ratio, or dissolved individually in water miscible organic solvents, and than combined with the β-lactoglobulin solution to achieve the desired ratio. In alternative embodiments, two or more different bioactive compounds may be bound to a single β-lactoglobulin protein. In alternative embodiments two or more bioactive compounds may be individually bound to the β-lactoglobulin protein and then the β-lactoglobulin:bioactive compound solutions may be combined together.

According to one embodiment the pH of the solution is adjusted according to step (c) to a pH between 3.0 and 5.0 and preferably to a pH between 3.5 and 4.5 when the polysaccharide is an anionic polysaccharide. According to another embodiment the pH of the solution is adjusted according to step (c) to a pH between 5.0 and 7.0 and preferably to a pH between 5.5 and 6.5 when the polysaccharide is a cationic polysaccharide. According to another embodiment the colloidal dispersion of nanoparticles obtained in step (c) is further filtered. According to another embodiment the colloidal dispersion of nanoparticles obtained in step (c) is further centrifuged.

According to another aspect, the present invention provides compositions comprising dehydrated nanoparticles according to embodiments of the present invention. The nanoparticles of the invention may advantageously be dried or lyophilized using any of the methods known in the art. The dried nanoparticles may conveniently be used as pharmaceutical or nutraceutical compositions per se or may be reconstituted in a suitable liquid medium prior to use. These and other embodiments of the present invention will be better understood in relation to the figures, description, examples and claims that follow. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
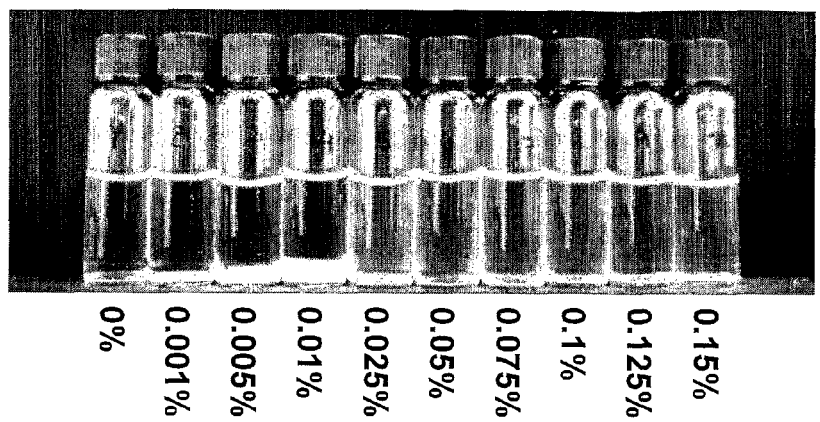
FIG. 1: The influence of pectin concentration on the colloidal stability of β-lactoglobulin:pectin complexes at pH 4, with β-lactoglobulin concentration of 0.05% w. β-lactoglobulin and pectin stock solutions were mixed, and the obtained solutions (pH 6.7-5.5 depending on the pectin concentration) were titrated to pH 4, and left over night at room temperature.

The present invention discloses a novel nano-encapsulation technology for harnessing β-lactoglobulin and ionic polysaccharides to form stable colloidal dispersion of nanoparticles for delivery of hydrophobic biologically active molecules via food products, including clear beverages.

As used herein, the term "nanoparticles" refers to particles with a mean diameter between 20-500 nm, typically the nanoparticles of the present invention have a mean diameter below about 400 nm; preferably, below about 300 nm; preferably below about 200 nm; more preferably below about 150 nm, even more preferably the mean diameter of nanoparticles of the invention is of about 100 nm or smaller. As well, the term "nanoparticles" refers herein to particles that form spontaneously by electrostatic forces and are colloidally stable, having absolute zeta potential values, (|ζ|), equal to or greater than 20 mV, preferably, equal or greater than 30 mV, more preferably, equal or greater than 35 mV, even more preferably, equal or greater than 40 mV.

As used herein, the terms "transparent" and "clear" are interchangeable. According to some embodiments, a clear solution is one in which the turbidity is less than or equal to 0.25; preferably, less than or equal to 0.2; preferably, less than or equal to 0.15; preferably, less than or equal to 0.1. As used herein, "turbidity" refers to a measurement quantifying the degree to which light traveling through the system is absorbed or scattered by the suspended particles. The scattering of light increases with the size of the particles, and their concentration. Turbidity is measured as the absorbance at 600 nm.

Typical embodiments of the present invention provide colloidally stable aqueous nanoparticle dispersions with turbidity levels below 0.25; preferably, below 0.2; more preferably, below 0.15; even more preferably, less than or equal to 0.1. At these turbidity levels the nanoparticles solutions are quite clear, and adequate for addition to clear fruit juices, soft drinks and other transparent and non-transparent low-fat and non-fat food products and beverages.

In special cases, like mineral water, where an even lower turbidity threshold is required, e.g. 0.05, an additional step of removing a small fraction of large particles by filtration and/or centrifugation may be added, yielding average particle size below 80 nm.

β-lactoglobulin, the major whey protein of cows' milk is a highly soluble protein. The present invention discloses that when β-lactoglobulin is mixed with an ionic polysaccharide, under conditions disclosed in this invention, nanoparticles (typical mean size 100 nm) are spontaneously formed, producing a transparent dispersion. These spontaneously formed electrostatic nanometric sized complexes, (nanocomplexes) have an absolute value of zeta potential greater than 20 mV; preferably greater than 30 mV; more preferably greater than 40 mV indicating their high colloidal stability and require no additional stabilizing agents. It is disclosed herein that the electrostatic nanoparticles neither require nor include any non natural ionic gelling or cross-linking agents such as for example sodium tripolyphosphate for their formation, stability, transparency or any other characteristic disclosed in the present invention.

Further disclosed herein, the present invention is based in part on the unexpected discovery that the desirable parameters of transparency and stability were retained in the colloidally stable dispersion of β-lactoglobulin-polysaccharide nanoparticles encapsulating hydrophobic biologically active compounds, thereby providing clear dispersions of nanoparticles encapsulating hydrophobic biologically active compounds that can be added to food products without adversely affecting the products' sensory characteristics of flavor and appearance.

Also disclosed herein, is that β-lactoglobulin-polysaccharide nanoparticles encapsulating hydrophobic biologically active compounds, afford protection to hydrophobic biologically active compounds against oxidation and degradation, thereby demonstrating that the present invention provides compositions and methods for protecting the hydrophobic biologically active compounds delivered via food products so that the health benefit of hydrophobic biologically active compounds may be realized.

As disclosed herein, an aspect of the present invention provides a colloidally stable dispersion of nanoparticles comprising β-lactoglobulin, a polysaccharide and at least one biologically active compound selected from the group consisting of a vitamin, a nutraceutical and a pharmaceutical.

As used herein, "β-lactoglobulin", refers to the protein β-lactoglobulin obtained from natural sources or produced by recombinant methods. Naturally occurring sources of β-lactoglobulin include skim milk, whole milk, and whey. β-lactoglobulin can be from any mammalian species of origin which is expressing the protein, preferably from a ruminant species, more preferably of bovine origin. Moreover, the β-lactoglobulin used should preferably be in its native state, rather than denatured and/or aggregated. The term "isolated β-lactoglobulin" includes β-lactoglobulin variants, including but not limited to β-lactoglobulin A and β-lactoglobulin B and their mixtures. It is known that β-lactoglobulin can exist as a monomer or form higher-order structures such as dimers and octomers. Complexes between β-lactoglobulin and a polysaccharide with or without a hydrophobic biologically active molecule according to the present invention can contain β-lactoglobulin monomers, dimers, octomers, or a mixture of these forms. Furthermore, the term "β-lactoglobulin" includes fragments of the β-lactoglobulin molecule that retain the ability to bind hydrophobic biologically active molecules. Preferably, the "isolated β-lactoglobulin" is substantially free of other proteins. In one embodiment, the "β-lactoglobulin" according to the present invention is at least 80% pure. In another embodiment, it is at least 85% pure. In another embodiment, it is at least 90% pure. In another embodiment, it is at least 95% pure.

Polysaccharides

"Saccharide" refers to any simple carbohydrate including monosaccharides, monosaccharide derivatives, sugars, including those, which form the individual units in a polysaccharide. "Monosaccharide" refers to polyhydroxyaldehyde (aldose) or polyhdroxyketone (ketose) and derivatives thereof.

"Polysaccharide" refers to polymers formed from about 50 to over 100,000 saccharide units linked to each other by hemiacetal or glycosidic bonds. The polysaccharide may be either a straight chain, singly branched, or multiply branched wherein each branch may have additional secondary branches, and the monosaccharides may be standard D- or L-cyclic sugars in the pyranose (6-membered ring) or furanose (5-membered ring) forms such as D-fructose and D-galactose, respectively, or they may be cyclic sugar derivatives, for example amino sugars such as D-glucosamine, deoxy sugars such as D-fucose or L-rhamnose, sugar phosphates such as D-ribose-5-phosphate, sugar acids such as D-galacturonic acid, or multi-derivatized sugars such as N-acetyl-D-glucosamine, N-acetylneuraminic acid (sialic acid), or N-sulfato-D-glucosamine. When isolated from nature, polysaccharide preparations comprise molecules that are heterogeneous in molecular weight. Polysaccharides include, among other compounds, galactomanans and galactomannan derivatives; galacto-rhamnogalacturons and galacto-rhamnogalacturon derivatives, and galacto-arabinogalacturon and galacto-arabinogalacturon derivatives.

In some embodiments, the average MW of the polysaccharide is at least 10 kDa; alternatively, the average MW of the polysaccharide is at least 15 kilodalton (kDa); alternatively, the average MW is at least 20 kDa; alternatively, the average MW is at least 50 kDa; Alternatively, the average MW is not greater than 200 kDa; alternatively, the average MW is not greater than 120 kDa; alternatively, the average MW is between 10-200 kDa; alternatively, the average MW is between 10-120 kDa.

The polysaccharides used according to embodiments of the present invention are selected from anionic polysaccharides and cationic polysaccharides. According to some embodiments of the present invention the polysaccharides are naturally-occurring. According to other embodiments the polysaccharides are synthetic polysaccharide. As used herein 'synthetic polysaccharides' refer to chemically or enzymatically modified polysaccharides, specifically relevant to the present invention are polysaccharides modified to carry a charged group such as carboxylate group, sulphate group and amine or imine groups. Non limiting examples of synthetic polysaccharides can be found in U.S. Pat. No. 6,528,497 and in Okada M. et al. Polymer journal, 15 (11); 821-26 (1983). Preferably, the polysaccharides of the present invention are naturally occurring polysaccharides.

An unlimited list of anionic polysaccharides according to embodiment of the present invention includes the group consisting of the group consisting of exudate gums (Arabic gum, ghatti gum, karaya gum, and tragacanth gum), pectins (high methoxy pectin, low methoxy pectin and amidated pectin, agaropectin, aloe pectin), microbial gums (xanthan, curdlan, pullulan, gellan, scleroglucan, welan, rhamsan), modified celluloses (sodium carboxymethyl cellulose), modified starches (carboxymethyl starch) and seaweed hydrocolloid extracts (sodium alginate, propyleneglycol alginate, ammonium alginate, alginic acid, carageenans (iota carageenan, kappa carageenan and lambda carageenan)), guar gum derivatives (carboxymethyl guar gum, carboxymethyl(hydroxypropyl) guar gum), okra gum, flaxseed saccharide (acidic), colominic acid, sulfated cellulose, hyaluronic acid, keratin sulfate, dermatan sulfate and chondroitin sulfate.

An unlimited list of cationic polysaccharides according to embodiment of the present invention includes the group consisting of diethylaminoethyl dextran, guar gum derivatives (such as guar hydroxypropyltrimonium chloride), quaternary nitrogen-containing cellulose ethers (some examples of which are described in U.S. Pat. No. 3,962,418), copolymers of etherified cellulose, guar and starch, cationic cellulose (some examples of which are described in U.S. Pat. No. 3,958,581), modified cationic cellulose polymers (such as polyquaternium 4, polyquaternium 10, polyquaternium 24 and polyquaternium 28), laurdimonium hydroxypropyl oxyethyl cellulose, steardimonium hydroxyethyl cellulose chitosan and derivatives thereof. According to some other embodiments the cationic polysaccharides include any polysaccharide carrying an amino group or an imine group.

Bioactive Compounds

As used herein, the term "bioactive compound" refers to a compound having a therapeutic, nutritional, disease-preventive. Bioactive compounds according to the teaching of the present invention include, but are not limited to vitamins, plant extracts, fruit and vegetable extract, antioxidants, lipids, steroids, phytochemicals, drugs, peptides, proteins, amino acids, proteoglycans, glycoproteins, hormones, polynucleotides or nucleic acids and anti-microbials. According to some preferred embodiments of the present invention, the bioactive compound is a hydrophobic compound.

The term "hydrophobic" or "hydrophobic compound" as used herein refers to compounds having a greater solubility in organic solvents of low polarity, such as long chain alcohols, than in aqueous solution. "hydrophobic" means "water-hating" and is used herein to indicate poorly soluble in water and soluble in non-polar solvents. The formulations described by the present invention facilitate solubilization of hydrophobic compounds which readily dissolve in organic solution such as alcohols. Preferably, the hydrophobic compound is insoluble in aqueous solution. It is to be explicitly understood that the organic solutions in which the hydrophobic bioactive compounds are dissolved should be water-miscible, preferably natural and have food grade purity. As used herein, 'food grade purity' refers to products which meet the strength specifications and maximum impurity limit indicated in the Food Chemicals Codex (FCC).

As used herein, the term "vitamin" refers to an organic compound required as a nutrient in tiny amounts by an organism. A compound is called a vitamin when it cannot be synthesized in sufficient quantities by an organism, and must be obtained from the diet. Vitamins usually have a 'recommended daily allowance' (RDA). In certain embodiments, the present invention relates to vitamins selected from the group consisting of: vitamin A, vitamin D, vitamin E and vitamin K. According to other embodiments, the present invention relates to any other vitamin, salts and derivatives thereof known in the art. According to other embodiments, the vitamins can be from any source known in the art. According to certain embodiments the vitamin D is selected from the group consisting of vitamin D2 (ergocalciferol), vitamin D3 (cholecalciferol) and any other vitamin D or its derivatives known in the art. According to other embodiments, the present invention relates to vitamin D salts and derivatives thereof. According to other embodiments, the vitamin E is selected from the group consisting of $\alpha$, $\beta$, $\gamma$, $\delta$-tocopherols and $\alpha$, $\beta$, $\gamma$, or $\delta$-tocotrienol and any other vitamin E known in the art. According to other embodiments, the present invention relates to vitamin E salts (e.g., vitamin E phosphate) and derivatives (e.g., tocopheryl sorbate, tocopheryl acetate, tocopheryl succinate, and other tocopheryl esters). According to additional embodiments, the vitamin A is selected from the group consisting of retinol, retinal, retinoic acid and any other vitamin A known in the art. According to other embodiments, the present invention relates to vitamin A salts and derivatives thereof. According to other embodiments, the vitamin K is selected from the group consisting of vitamin K1 (phytonadione), vitamin K2 (menaquinone), vitamin K3 (menadione), vitamin K4, vitamin K5, vitamin K6, vitamin K7, and their salts and derivatives.

As used herein, the term "nutraceutical" also known as a functional food, refers to any substance that is a food or a part of a food which promotes health or prevents disease or enhances well-being. Nutraceuticals do not necessarily have an official recommended daily allowance. Non limiting examples of nutraceuticals include antioxidants, phytochemicals, hormones, pantothenate, folic acid, pro-vitamins, Coenzyme Q10, essential and/or highly unsaturated fatty acids, and mid-chain triglycerides, nutritional supplements, enzymes such as amylases, proteases, lipases, pectinases, cellulases, hemicellulases, pentosanases, and phytases, pigments, oligopeptides, dipeptides, and amino acids, and mixtures thereof.

"Essential fatty acids" may refer to any fatty acid that may be utilized by the body, and included, without limitation, chemical chains of carbon, hydrogen, and oxygen atoms that are part of a fat (lipid), are a major component of triglycerides, which may be classified as either saturated, polyunsaturated, or monounsaturated, and may be found in nature or produced synthetically. They may include without limitation sterols such as cholesterol and derivatives thereof, prostaglandins, lecithin, choline, inositol, conjugated linolenic acid, myristic acid, palmitic acid, stearic acid, omega 3 fatty acids (for example: docosahexaenoic acid (DHA), eicosapentaenoic acid, $\alpha$-linolenic acid, stearidonic acid eicosatrienoic acid, eicosatetraenoic acid, docosapentaenoic acid and glycerol ester derivatives thereof), omega 6 fatty acids (for example: linoleic acid, gamma-linolenic acid, eicosadienoic acid, dihomo-gamma-linolenic acid, arachidonic acid, docosadienoic acid, adrenic acid, docosapentaenoic acid and calendic acid), omega 9 fatty acids (for example: oleic acid, eicosenoic acid, mead acid, erucic acid and nervonic acid), polyunsaturated fatty acids, long-chained polyunsaturated fatty acids, arachidonic acid, monounsaturated fatty acids, precursors of fatty acids, and derivatives of fatty acids.

"Antioxidants" may refer to any molecule capable of slowing or preventing the oxidation of other molecules. The antioxidants used according to embodiments of the present invention may include without limitation a racemic mixture of alpha.-lipoic acid, Vitamin C and its esters, green tea polyphenols, green tea extract, (−)-epigallocatechin-3-gallate, (−)-epigallocatechin-3-gallate, (−)-epigallocatechin, (−)-epicatechin, carotenoids ($\alpha$-, $\beta$-, and $\gamma$-carotene), curcuminoids such as curcumin (diferuloylmethane), desmethoxycurcumin (hydroxycirmamoyl feruloylmethane), and bis-desmethoxycurcumin (dihydroxydicinnamoyl methane), chlorophyllin and/or its salts, superoxide dismutase, glutathione peroxidase, tocotrienols, polyphenols, cysteine, and methionine.

"phytoestrogens" or "dietary estrogens" as used herein refer to any naturally occurring non steroidal plant compounds possessing estrogenic activity. Non limiting examples of phytosterols include isoflavones (for example: genistin, genistein, daidzein, daidzin, malonyl daidzin, glycitin, malonyl glycitin, acetyl glycitin, acetyl daidzin, acetyl genistin, glycitein, and mixtures thereof), stilbenoids (for example: trans-resveratrol), lignans (for example: pinoresinol, podophyllotoxin, steganacin, matairesinol, lariciresinol, secoisolariciresinol, hydroxymatairesinol, syringaresinol and sesamin) and coumestans (for example: coumestrol, wedelolactone, plicadin), beta-sitosterol, campesterol, ergosterol (provitamin D2), brassicasterol, delta-7-stigmasterol and delta-7-avenasterol.

Other nutraceticals may include fruit and vegetable extracts; phospholipids, (e.g. phosphatidyl-serine); proteoglycans (for example: decorin, biglycan, fibromodulin and lumican), certain amino acids (for example: iso-leucine, leucine, methionine, phenylanine, tryptophan, and valine); food additives, phytonutrients (for example, lutein, zeaxanthin and astaxanthin), plant oils; fish and marine animal oils and algae oils.

The term "pharmaceutical" as used herein refers to a medicinal drug. According to some preferred embodiments the pharmaceutical associated with the nanoparticles of the present invention is hydrophobic. According to other preferred embodiments, the nanoparticles of the present invention can encapsulate a wide range of classes of drugs which suffer from poor oral or other mucosal membrane absorption, and hence bioavailability, which severely limits their applicability, usage and effectiveness. Such pharmaceuticals may optionally comprise any type of hydrophobic, insoluble in an aqueous solution and/or at body pH values, and/or pH sensitive material, including without limitation plant alkaloids and the like, drugs with multi-cyclic ring structures (including those that lack polar groups), peptides and proteins, including antibodies and enzymes, or any type of biopolymer, including without limitation oligonucleotides, polynucleotides (including without limitation siRNA molecules and the like) and chemotherapeutic drugs, which include any drug having high systemic toxicity for treatment of cancer.

Non-limiting examples of such classes of drugs include non-steroidal anti-inflammatory drugs (NSAID) such as COX-2 inhibitors, ibuprofen, naproxen, diclofenac, indomethacin, piroxicam, etc., anti-resorptive agents such as bisphosphonates, steroids including corticosteroids, antivirals (acyclovir, IUdR, ganciclovir, vidarabine, AZT), steroidal anti-inflammatory drugs (dexamethasone, loteprednol, prednisolone derivatives, etc.), antibiotics (e.g., ampicillin and erythromycin), antifungals (e.g., miconazole), hormones, local anesthetics, analgesics, calcium channel blockers (e.g., Verapamil), prostaglandins and prostacyclins, cholinergics, adrenergic antagonists, anticonvulsants (e.g., phenyloin), antianxiety agents, major tranquilizers, antidepressants, anabolic steroids, estrogens, progesterones, immune suppressants such as cyclosporine, glycosaminoglycans (heparin, heparan, chondroitin sulfate, and low molecular weight derivatives thereof); any type of fluorescent dye, including but not limited to cyanines, indocyanines, or squaraines; antihelminthics, anti-arrhythmic agents, antibacterial agents, anti-viral agents, anti-coagulants, anti-diabetics, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-blockers, cardiac inotropic agents, corticosteroids, diuretics, anti-Parkinsonian agents, gastro-intestinal agents, histamine receptor antagonists, keratolyptics, lipid regulating agents, anti-anginal agents, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, anti-benign prostate hypertrophy agents, essential fatty acids, non-essential fatty acids; and combinations thereof, or derivative or salt thereof.

In addition to the above listed therapeutic agents, specific examples of therapeutic agents may optionally comprise one or more of acetretin, albendazole, albuterol, aminoglutethimide, amiodarone, amlodipine, amphetamine, amphotericin B, atorvastatin, atovaquone, atropine, azithromycin, baclofen, beclomethasone, benezepril, benzonatate, betamethasone, bicalutanide, bifonazole, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, clotrimazole, clindamycin, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, diphenhydramine, dirithromycin, donezepil, efavirenz, eprosartan, ergocalciferol, ergotamine, etodolac, etoposide, famotidine, fenofibrate, fentanyl, fexofenadine, finasteride, fluconazole, flurbiprofen, fluvastatin, fosphenyloin, frovatriptan, furazolidoneu, gabapentin, gemfibrozil, gentamicin, glibenclamide, glipizide, glyburide, glimepiride, griseofulvin, halofantrine, hydrocortisone, ibuprofen, iodoxuridine, irbesartan, irinotecan, isosorbide dinitrate, isotretinoin, itraconazole, ivermectin, ketoconazole, ketorolac, ketotifen, lamotrigine, lansoprazole, leflunomide, lidocaine, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, montelukast, nabumetone, nalbuphine, naratriptan, nelfmavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, phenyloin, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, sodium clodronate, spironolactone, sumatriptan, tacrine, tacrolimus, tamsulosin, targretin, tazarotene, telmisartan, teniposide, terbinafine, terazosin, tetracaine, tetracycline, tetrahydrocannabinol, tiagabine, ticlopidine, tirofibran, tizanidine, topiramate, topotecan, toremitfene, tramadol, tretinoin, triamcinolone, troglitazone, trovafloxacin, ubidecarenone, valsartan, venlafaxine, verapamil, verteporfin, vigabatrin, zafirlukast, zileuton, zolmitriptan, zolpidem, zopiclone, pharmaceutically acceptable salts, isomers, and derivatives thereof, and combinations thereof.

Non-limiting examples of suitable chemotherapeutic drugs include a taxane (e.g., paclitaxel), vincristine, adriamycin, vinca alkaloids (e.g., vinblastine), anthracyclines (e.g., doxoribicin), epipodophyllotoxins (e.g., etoposide), cisplatin, actinomycin D, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, camptothecin, cisplatin, metronidazole, Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Avastin, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cisplatin, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, hrinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, or Zoledronic acid, or combinations or derivative or salt thereof.

According to the present invention the compositions of the invention may further comprise excipients as are suitable for food products. Non-limiting examples of such agents include flavorants, fragrances preservatives and coloring agents. Exemplary flavonoids and flavonoid derivatives include 1,2, 3,6-tetra-o-gallyol-.beta.-d-glucose; 2'o-acetylacetoside; 3,3',4-tri-o-methyl-ellagic acid; 6,3',4'-trihydroxy-5,7,8-trimethoxyflavone; 6-hydroxy-luteolin; 6-hydroxykaempferol-3,6-dimethyl ether; 7-o-acetyl-8-epi-loganic acid; acacetin; acetoside; acetyl trisulfate quercetin; amentoflavone; apigenin; apiin; astragalin; avicularin; axillarin; baicalein; brazilin; brevifolin carboxylic acid; caryophyllene; chrysin-5,7-dihydroxyflavone; chrysoeriol; chrysosplenol; chrysosplenoside-a; chrysosplenoside-d; cosmosiin; .delta.-cadinene; dimethylmussaenoside; diacerylcirsimaritin; diosmetin; dosmetin; ellagic acid; ebinin; ethyl brevifolin carboxylate; flavocannibiside; flavosativaside; genistein; gossypetin-8-glucoside; haematoxylin; hesperidine; hispiduloside; hyperin; indole; iridine; isoliquiritigenin; isoliquiritin; isoquercitrin; jionoside; juglanin; kaempferol-3-rhamnoside; kaempferol-3-neohesperido side; kolaviron; licuraside; linariin; linarin;

lonicerin; luteolin; luetolin-7-glucoside; luteolin-7-glucoside; luetolin-7-glucoronide; macrocarpal-a; macrocarpal-b; macrocarpal-d; macrocarpal-g; maniflavone; methy scutellarein; naringenin; naringin; nelumboside; nepetin; nepetrin; nerolidol; oxyayanin-a; pectolinarigenin; pectolinarin; quercetagetin; quercetin; quercimertrin; quercitrin; quercitryl-2" acetate; reynoutrin; rhamnetin; rhoifolin; rutin; scutellarein; sideritoflavone; sophoricoside; sorbarin; spiraeoside; trifolin; vitexin; and wogonin.

Food Compositions and Beverages

Combining a β-lactoglobulin-polysaccharide nanoparticle encapsulating a bioactive compound according to the present invention, with other food ingredients forms the presently claimed food compositions and beverages. Alternately stated, a food composition or beverage is a food product or beverage containing a β-lactoglobulin-polysaccharide nanoparticle encapsulating at least one biologically active compound according to the present invention. Alternately stated, a food composition or beverage is a food product or beverage containing a β-lactoglobulin-polysaccharide nanoparticle encapsulating at least one biologically active compound prepared according to the methods of the present invention.

A food composition can be a liquid or a solid food for human or animal consumption. Solid food products include, but are not limited to, dairy products, processed meats, baked products, processed vegetables, processed fruits, dietary supplements including vitamins and nutrient supplements and pharmaceuticals. Liquid food products include, but are not limited to dairy and non-dairy beverages, dairy and non-dairy beverage concentrates, dairy substitutes including infant formulas, dietary supplements including vitamin and nutrient supplements and pharmaceuticals.

In preferred embodiments of the invention, the disclosed β-lactoglobulin-polysaccharide nanoparticles encapsulating a biologically active compound, according to the present invention, are used as a food additive to fortify and enrich foods, more preferably low-fat and non-fat foods.

As defined herein "low-fat" indicates a food having equal to or less than 5%, 3%, 2%, 1%, 0.5%, 0.1% or even 0.01% (w/w) fat and includes "non-fat foods or beverages". "Non-fat foods or beverages" are defined as those having essentially no fat therein (or only a negligible amount), such as skim milk. Alternatively, a low-fat food is one that has a reduced amount of fat as compared to what is normally found in the food or beverage. Thus, for example, a low-fat ice cream may have greater than 5% (w/w) fat, but it has less fat than is normally found in ice cream (usually at least ⅓ less).

To deliver nanoparticles encapsulating hydrophobic biologically active compounds via food products and beverages, including low-fat and non-fat food products, the nanoparticles need to be stable. In certain aspects of this invention, nanoparticles comprising β-lactoglobulin, a polysaccharide and at least one encapsulated hydrophobic biologically active compound are stable at pH values of about pH=4 when anionic polysaccharides are used and at about pH=6 when cationic polysaccharides are used.

Formation of β-Lactoglobulin/Polysaccharide Nanocomplexes

Complexes of β-lactoglobulin with anionic polysaccharides such as pectin are preferably formed below the pI of the protein (pI=5.18) (Jameson et al., 2002, *Int. Dairy J.*, 12; 319), where the protein is positively charged. To obtain stable nanometric complexes, it is important to form complexes with a large net charge, so that their repulsion will keep them from aggregating and precipitating. Furthermore, to obtain such charged nanoparticles, one of the two interacting biopolymers has to be in excess. To obtain protection of the biologically active compound bound within the protein, below the pI, the polyanion should be in excess. To achieve that, different ratios of low methoxyl pectin and β-lactoglobulin were studied, and the pectin-to-protein ratio range selected in which the particles would be small enough (<200 nm, more preferably <100 nm) and the zeta potential sufficiently negative (≥|40|) so that the system will have the desirable properties of stability and transparency. Exemplary embodiments of the present invention provide acidic nanoparticle solutions in which the weight percentage of pectin in solution is in the range of 0.07% wt-0.15% wt given the β-lactoglobulin weight percentage is 0.05%.

The pH range can affect particle size and turbidity. In typical embodiments, with or without the addition of a biologically active compound, using the exemplary polysaccharide, pectin, this apparently results from the fact that as the pH rises towards the pI of β-lactoglobulin, the positive charge of the protein decreases and the negative charge of the pectin increases. Consequently, the complexes become more negative resulting in larger repulsion between them and dissociation into smaller and more stable nanoparticles (also referred to as nanocomplexes). According to one embodiment of the present invention, the pH range used in the formation of nanocomplexes comprising β-lactoglobulin and an anionic polysaccharide, with or without a biologically active compound, is between pH 3.5 and pH 4.5. Alternatively, the pH is less than the pI of the protein by at least 0.5 pH units but not more than 2.0 pH units.

The present invention further provides methods for the preparation of colloidally stable dispersions of nanoparticles comprising β-lactoglobulin and a cationic polysaccharide.

Two possibilities were considered in finding proper conditions for the formation of nanoparticles comprising β-lactoglobulin and a cationic polysaccharide such as chitosan. If the β-lactoglobulin was mixed with the chitosan at a pH that is far below the pI of the protein, both the protein and the chitosan would be positively charged, and will therefore repel each other, thus forming a homogeneously mixed solution at low to moderate concentrations. Upon graduate increase of the pH while stirring, to a pH which is optimal for complex formation, β-lactoglobulin and chitosan complexes would form, and given sufficient excess of chitosan, the complexes formed would be as small and stable as possible.

Figure 8:
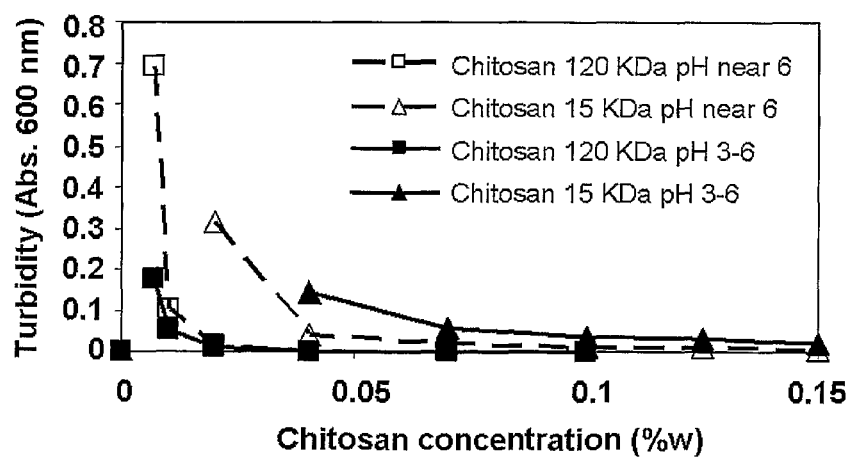
FIG. 8: Turbidity of solutions versus chitosan concentration for two types of chitosan (120 kDa and 15 KDa) using two methods of mixing β-lactoglobulin with chitosan.
Figure 9:
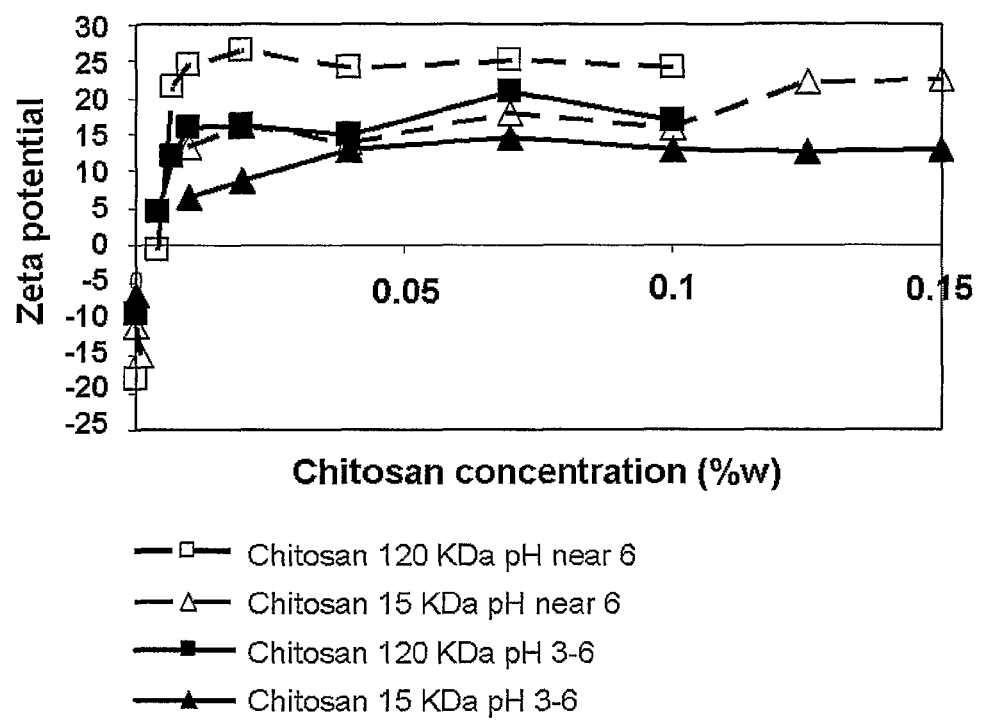
FIG. 9: Zeta potential of solutions versus chitosan concentration for two types of chitosan (120 kDa and 15 KDa) using two methods of mixing β-lactoglobulin with chitosan.
Figure 10:
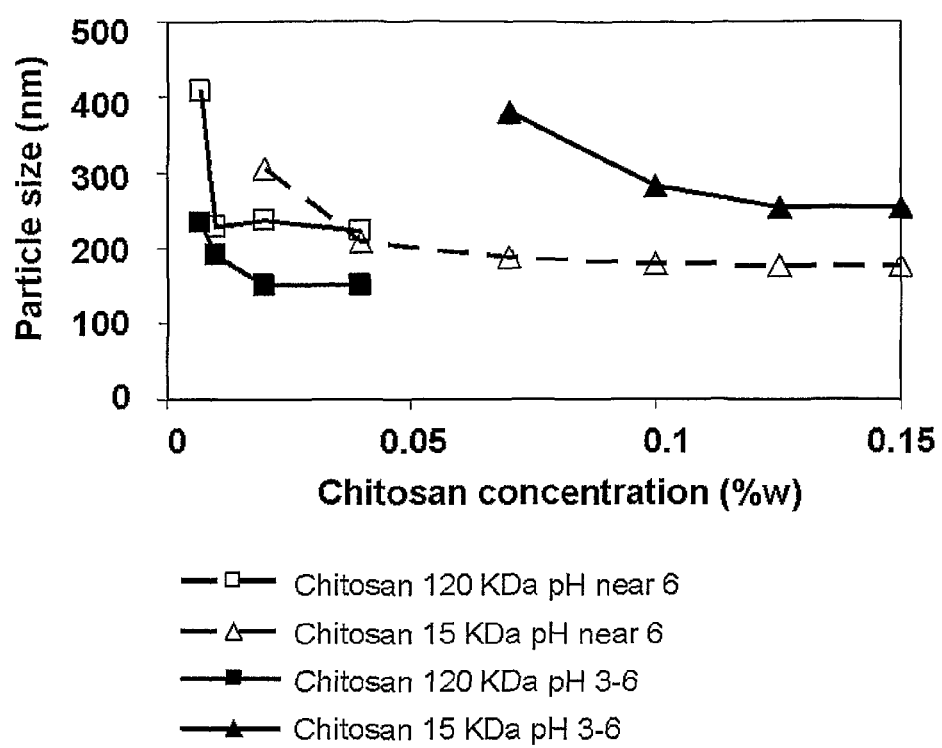
FIG. 10: Particle size of solutions versus chitosan concentration for two types of chitosan (120 kDa and 15 KDa) and the two methods of mixing β-lactoglobulin with chitosan.

According to one exemplary embodiment of the present invention, the formation of the nanoparticles comprising β-lactoglobulin and chitosan was done by mixing both protein and polysaccharide at pH 3.0, where they mutually repel, followed by raising the pH to 6.0 to induce complexation (see FIGS. 8, 9 and 10, labeled: 'pH 3-6'). According to another embodiment of the present invention, the β-lactoglobulin and chitosan were mixed directly at a pH of around 6, followed by adjustment of the pH to 6.0 (see FIGS. 8, 9 and 10, labeled: 'pH near 6'). In another embodiment, two different molecular weights of the cationic polysaccharide were compared, 120,000 Da, and 15,000 Da. When a 15,000 Da chitosan was used and the mixing was done at a pH close to 6 followed by adjustment of the pH to 6.0 particles with a mean diameter lower than 200 nm were obtained. Interestingly, when a chitosan of 120,000 Da was used and the mixing was done at pH 3 followed by adjustment of the pH to 6.0, particles with a mean diameter lower than 200 nm were obtained. In another embodiment, the optimal pH for the formation of nanoparticles comprising β-lactoglobulin and a cationic polysaccharide is greater than the pI of βlactoglobulin by at least 0.3 pH (e.g. >5.5) units but not more than 2 pH units (e.g. <7.2). In preferred embodiments of the present invention, the pH of the solution comprising nanoparticles of β-lactoglobulin and a cationic polysaccharide is in the pH range of 5.8 and 6.50.

It is to be explicitly understood that the complex stability depends also on the ionic strength of the solution (Schmitt et al., 1998, *Critical Reviews in Food Science and Nutrition* 38, 689). As the ionic strength of the solution increases upon addition of salt, the stability of the complexes decreases due to the screening of the electrostatic charges.

Preservation of the integrity and functionality of the hydrophobic biologically active compounds is essential for receiving the health benefit of food products enriched with these compounds. The main degradation mechanisms expected for many hydrophobic biologically active compounds are oxygen and UV light induced oxidation. The β-lactoglobulin/polysaccharide nanoparticles of the present invention effectively confer protection to the bioactive compound as compared to the protection of the bioactive compound when encapsulated by the β-lactoglobulin protein only. Without wishing to be bound by theory or mechanism of action, this may be due to the fact that the bioactive compound is immobilized by the protein and shielded by the protein-polysaccharide complex and hence its reactivity is reduced, and so is the accessibility of oxidizing agents to the encapsulated bioactive compound.

Pharmaceutical Compositions

According to another embodiment, the present invention provides a pharmaceutical composition comprising a dispersion of nanoparticles according to embodiments of the present invention and a pharmaceutically acceptable excipient.

As used herein, a "pharmaceutical composition" refers to a preparation of one or more of the dispersions of nanoparticles comprising β-lactoglobulin, polysaccharide and a bioactive compound selected from a vitamin, a nutraceutical and a pharmaceutical. The purpose of a pharmaceutical composition is to facilitate administration of the bioactive compound to a subject.

Herein, the term "excipient" refers to an inert substance added to a pharmaceutical composition to further facilitate administration of a bioactive compound. Examples, without limitation, of excipients include calcium carbonate, calcium phosphate, various sugars, starch and cellulose and their nonionic derivatives, gelatin, vegetable oils, and polyethylene glycols.

According to another embodiment, the present invention provides a pharmaceutical composition comprising dehydrated (dried and/or lyophilized) nanoparticles comprising β-lactoglobulin, polysaccharide and a bioactive compound selected from a vitamin, a nutraceutical and a pharmaceutical and a pharmaceutically acceptable aqueous carrier, excipient or diluent. Examples of pharmaceutically acceptable aqueous carriers include, but are not limited to water, phosphate buffered saline, Ringer's solution, dextrose solution, serum-containing solutions, Hank's solution, other aqueous physiologically balanced solutions. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Pharmaceutical compositions of the present invention can be sterilized by conventional methods.

The compositions of the present invention may further comprise any other bioactive compound which is not encapsulated by the β-lactoglobulin/polysaccharide nanoparticles of the invention. Preferably, such additional bioactive compound is water soluble. Alternatively, the additional bioactive compound may be associated/encapsulated/bound to any delivery agent which is other than the β-lactoglobulin/polysaccharide nanoparticles of the invention.

The following Examples are provided to illustrate the present invention, and should not be construed as limiting thereof. One skilled in the art can readily devise many variations and modifications of the principles disclosed herein without departing from the scope of the invention.

EXAMPLES

Materials

Bovine β-lactoglobulin isolate was obtained from Davisco Food International, Inc. (Eden Praire, Minn. USA), dialyzed against de-ionized water and freeze-dried. An experimental sample of low molecular weight (MW≈20,000 Da) low methoxy pectin with a degree of esterification of 5-10% was kindly provided by CP-Kelco (Atlanta, Ga. USA). Chitosan with a molecular weight (MW) of 50-190 kDa (average 120 kDa), 90% pure, 84.5% deacetylated was purchased from Sigma-Aldrich (Rehovot, Israel). Chitosan with a MW of 15±0.5 kDa, 85% deacetylated, was kindly donated by Marine Science Co., Ltd (Japan). Vitamin $D_2$ and DHA were purchased from Sigma-Aldrich.

Solution Preparation

β-lactoglobulin (0.2% wt) and 20 kDa low methoxyl pectin (1% wt) solutions were freshly prepared in filtered doubly distilled water and stirred for at least 6 hours for complete hydration. The protein and pectin stock solutions were filtered using a 0.22 μm filter. A 276 μL aliquot of a 5 mg mL$^{-1}$ solution of vitamin $D_2$ (Sigma-Aldrich, Rehovot, Israel) in absolute ethanol (Sigma-Aldrich, Rehovot, Israel) was added per 100 mL protein solution while stirring, where vitamin encapsulation was studied.

The 120 kDa, 84.5% deacetylated chitosan is only soluble in an acidic environment. Therefore, the chitosan was dissolved in 5 mM acetic acid solution and titrated to pH 3 with HCl in order to achieve full dissolution. 15 kDa chitosan, 85% deacetylated was dissolved either in filtered doubly distilled water or in 5 mM acetic acid.

Vitamin $D_2$ was analytically weighed and dissolved in a measured volume of absolute ethanol. The ethanolic vitamin solution was prepared and maintained in the dark. It was then added to the protein solution while stirring at pH≈6.8, then stirred further for 30 min.

DHA volume was measured with a calibrated analytical glass syringe, and dissolved in a measured volume of absolute ethanol by stirring in dark conditions. The DHA solution was kept refrigerated under nitrogen or argon in sealed vials, for a minimal time before addition to the protein solution.

Evaluation of the Binding of Hydrophobic Bioactive Compounds to β-Lactoglobulin

The binding of lipophilic ligands to β-lactoglobulin was characterized by fluorometric titration using Fluorolog 3-22, Jobin Yvon, Horiba spectrofluorometer, at 25° C. Binding was followed by measuring the binding-induced quenching of the intrinsic fluorescence of the tryptophanyl residue, Trp19, found in the hydrophobic β-barrel of β-Lg, using excitation and emission wavelengths of 287 and 332 nm respectively (Cogan, U.; Kopelman, M.; Mokady, S.; Shinitzky, M., 1976, *European Journal of Biochemistry*, 65: 71-8). For example, 1 μM β-Lg solutions at pH 7.0 in 100 mM Trizma base were titrated with 2-10 μl incremental aliquots of 0.2 μM DHA dissolved in ethanol.

Methods for Evaluating β-Lactoglobulin-Polysaccharide Complexes

Four criteria were used in order to evaluate the β-lactoglobulin-polysaccharide nanocomplexes and find the conditions (pH and ratio) which yield transparent suspensions containing small and stable nanoparticles: Sedimentation—Qualitative observation of the solutions in glass vials, following overnight equilibration at room temperature; Turbidity—Measured by an Ultrospec 3000 spectrophotometer (GE Healthcare, Life Sciences, UK), at 600 nm using 1 cm path cuvettes: Samples were vortexed prior to analysis; Electrophoretic mobility (EM or μe)—Measured using a zeta potential/particle size analyzer NICOMP™ 380 (Particle Sizing Systems Ltd. Santa Barbara, Calif., Agilent Technologies Inc., USA). The EM was measured under a 3 V/cm e-field at 25° C.; and Particle size—measured by Dynamic Light Scattering using the NICOMP™380 at 23° C. using 0.933 cp for the viscosity of the medium. Mean diameter (Gaussian approximation) was only determined in solutions that showed no sedimentation after overnight equilibration.

Statistical analysis, and non-linear model-fit was performed using JMP© software, (SAS Institute, Cary, N.C., USA). Error bars given in the graphs represent standard error. Analyses were typically performed in duplicate or in triplicate.

Example 1

β-Lactoglobulin-Pectin Electrostatic Complex Formation

A series of solutions containing a constant protein concentration (0.05% wt) and varying pectin concentrations (0-0.15% wt) were prepared by adding different amounts of 0.2% wt stock polysaccharide solution to the protein solution. These solutions were titrated to the desired pH, using HCl, than stirred for 1 hr and stored overnight at room temperature prior to analysis.

Figure 2:
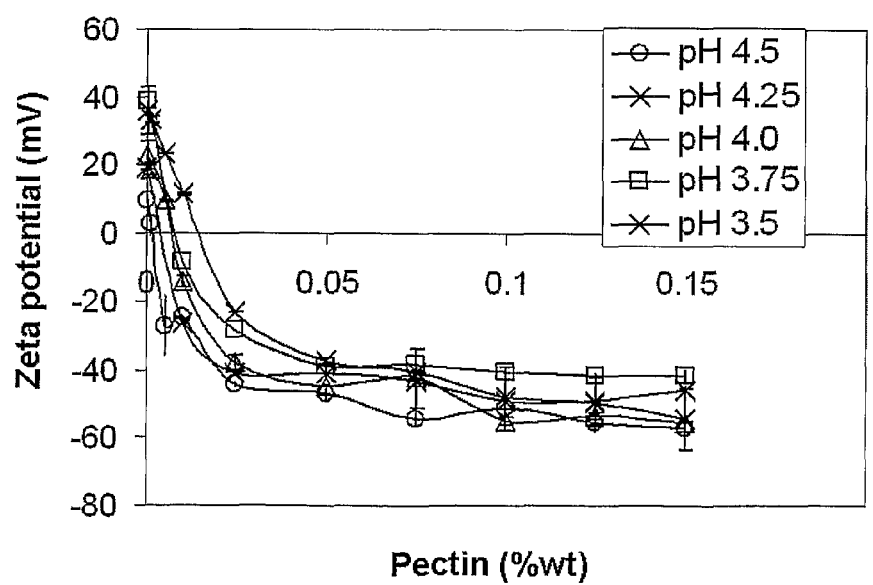
FIG. 2: Influence of pectin concentration on zeta potential of 0.05% wt β-lactoglobulin solutions and the effect of pH in the range 3.5 to 4.5.
Figure 3:
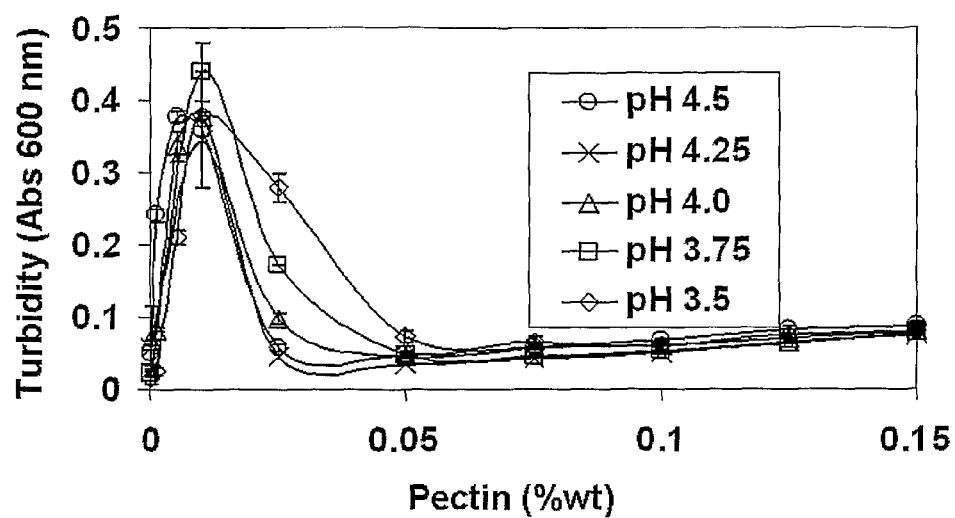
FIG. 3: Turbidity of β-lactoglobulin-pectin dispersions as a function of pectin concentration at different pH values. β-lactoglobulin concentration was 0.05% w in all samples. Turbidity was measured at 600 nm after an over-night equilibration at room temperature. Samples were vortexed immediately before measurement.

FIG. 1 shows the visual sedimentation observation results, 24 hrs after mixing the biopolymer solutions and slowly adjusting the pH to 4.0 while stirring. β-lactoglobulin concentration was 0.05%. The results of the ratio scan at pH 4.0 indicated that when β-lactoglobulin concentration was kept constant at 0.05% wt, the pectin percentage range that provided the desired properties of transparency and stability was above 0.025% wt pectin (FIG. 1-3). As pectin concentration was increased from 0.001 to 0.01% wt, more and more coacervation occurred (i.e. neutral colloidal complexes aggregated and were held together by electrostatic as well as van der Waals attractive forces), resulting in increased precipitation. However, at 0.025% wt pectin and beyond, only soluble complexes were formed, yielding stable transparent dispersions. FIG. 3 shows the influence of pectin concentration on turbidity of 0.05% wt β-lactoglobulin solution at various pH values (3.5 to 4.5). A sharp rise was observed as pectin concentrations were increased to about 0.007% wt pectin, but beyond this concentration, the turbidity decreased rapidly, to very low values (<0.05) above 0.05% wt pectin. For submicron particles, whose movement is dominated by Brownian motion, very good colloidal stability is generally obtained when $|\zeta| \geq 40$ mV, as the repulsion between colloidal particles is sufficiently large to keep them from aggregating. FIG. 2 depicts the zeta potential of the 0.05% wt β-lactoglobulin solutions as a function of pectin concentration at various pH values (3.5 to 4.5). As pectin concentration increased, the zeta potential decreased from +6 mV (pure β-lactoglobulin), to about −40 mV above 0.05% wt pectin, passing 0 mV (minimal stability) around 0.01% wt pectin. This is in accord with the maxima of turbidity (FIG. 3) and precipitation (FIG. 1).

Example 2

Figure 4:
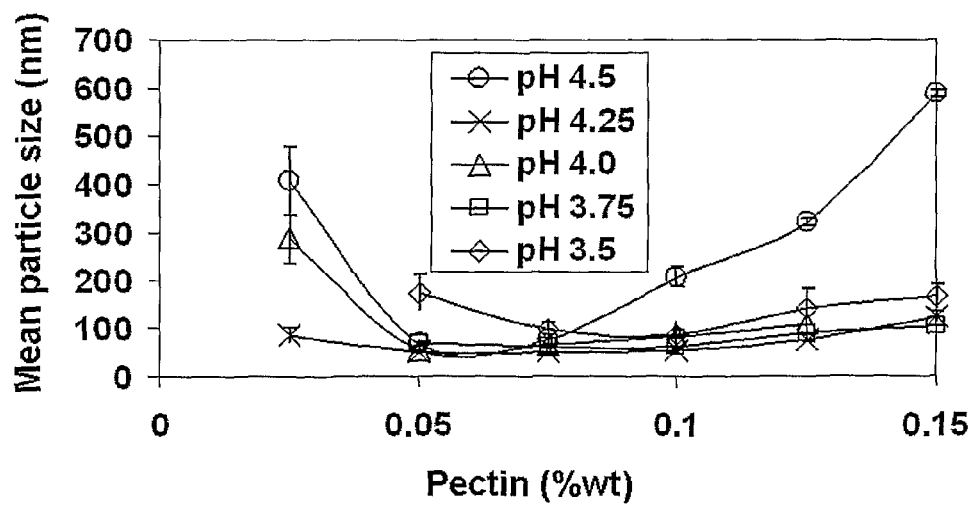
FIG. 4: Mean particle size in β-lactoglobulin-pectin dispersions as a function of pectin concentration at different pH values. β-lactoglobulin concentration was 0.05% w in all samples. Particle size was measured in the non-sedimented samples after an over-night equilibration at room temperature.
Figure 5:
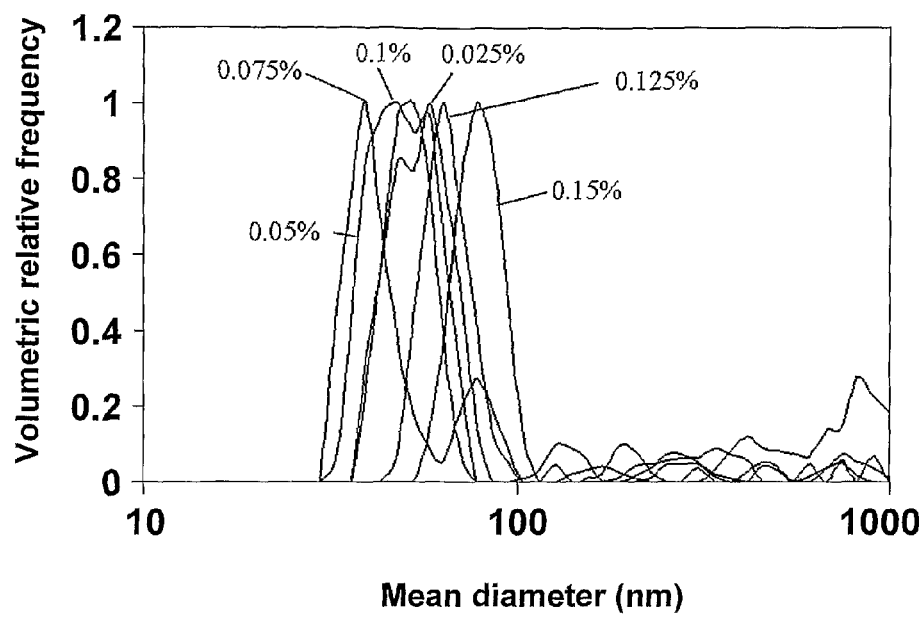
FIG. 5: Particle size distribution in β-lactoglobulin-pectin dispersions with different pectin concentrations (% w). β-lactoglobulin concentration was 0.05% w and the pH was 4.25. Particle size distribution was measured after an over-night equilibration at room temperature. The y axis being 'volumetric relative frequency' refers to a volume-weighted distribution which is normalized according to the highest peak, defined as 1 for each sample.

The Effect of pH on Particle Size and Turbidity of β-Lactoglobulin-Pectin Complexes The effect of pH on particle size and turbidity was studied in the range $3.5 \leq pH \leq 4.5$. Pectin concentrations were maintained within the range used in Example 1. FIG. 3 shows the influence of pectin concentration on turbidity of 0.05 wt β-lactoglobulin solution at the studied pH range. The effect of pH on turbidity was most notable between 0.001 and 0.05% wt pectin. In this range, as the pH increased from 3.5 to 4.25 the turbidity decreased. FIG. 4 shows that for most pH values, size was minimal between 0.05% and 0.075% pectin. Table 1 shows the minimal mean particle size of the β-lactoglobulin-pectin complexes at the different pH studied and the pectin concentration at these minima. The smallest mean particle size, 49 nm, was obtained at pH 4.25, and 0.075% wt pectin. Interestingly, at pH 4.5, closest to the pI of the protein, particle size was most strongly dependent on pectin concentration. When particle size was minimal, the distribution of particles was narrowest. FIG. 5 shows representative distribution curves of particle distribution at pH 4.25 and at several pectin concentrations.

TABLE 1

Minimal mean particle size of the β-lactoglobulin-pectin complexes at the pH levels studied.*

| pH | Pectin Concentration (% wt.) at Which the Minimal Mean Particle Size Was Obtained | Minimal Mean Particle Size (nm) |
|---|---|---|
| 3.5 | 0.075 | 88 ± 11 |
| 3.75 | 0.075 | 61 ± 2 |
| 4 | 0.05 | 55 ± 6 |
| 4.25 | 0.05 | 50 ± 4 |
|  | 0.075 | 49 ± 1 |
| 4.5 | 0.05 | 69 ± 3 |

*β-lactoglobulin concentration was 0.05%.

Example 3

Figure 6:
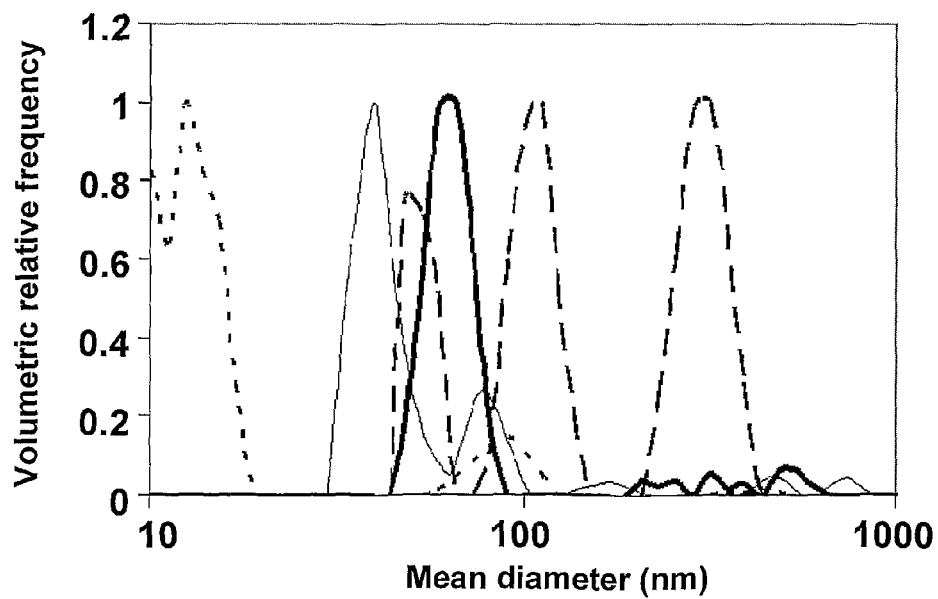
FIG. 6: Particle size distributions of: 0.05% w β-lactoglobulin only ( . . . ); vitamin D (0.027 mM) only (— —); complexes made with 0.05% w β-lactoglobulin, 0.05% w pectin and vitamin D (0.027 mM) (__) and complexes of 0.05% w β-lactoglobulin and pectin 0.05% w (without the vitamin) (__). All of the systems were titrated to pH 4.25.

Encapsulation of Vitamin $D_2$ in β-Lactoglobulin-Pectin Complexes and Effect on Particle Size Incorporation of vitamin $D_2$, as an exemplary fat-soluble vitamin, into β-lactoglobulin-pectin complexes necessitated binding vitamin $D_2$ to β-lactoglobulin prior to pectin addition. The vitamin was dissolved in absolute ethanol. A 276 μL aliquot of a 5 mg mL$^{-1}$ solution of vitamin $D_2$ in absolute ethanol was added, while stirring, to 100 mL of 0.2% wt β-lactoglobulin solution at pH≈6.8, then stirred further for 30 minutes. Pectin solution was then added to the β-lactoglobulin-vitamin D2 solution to final concentrations of 0.05% wt protein and 0.1% wt pectin, and the pH was adjusted to 4.0. The samples were stirred further for an hour. FIG. 6 shows the particle size distributions of: 0.05% wt β-Lg only; vitamin D (0.027 mM) only; complexes made with 0.05% wt β-Lg, 0.05% wt pectin and vitamin D (0.027 mM) and complexes of 0.05% wt β-Lg and pectin 0.05% wt (without the vitamin). All of the systems were titrated to pH 4.25.

To evaluate the encapsulation of the vitamin within the nanoparticles, the partition of the vitamin between the particles and the serum was studied. For this purpose, an ultra centrifuge (15,000×g) was used to separate the nanocomplexes (pellet) from the serum (supernatant), and the concentration of vitamin $D_2$ in the pellet was compared to that in the serum. Vitamin content of particles and serum was analyzed by solvent extraction followed by reversed phase HPLC, according to the method described in Semo et al., 2007, *Food Hydrocolloids* 21:936. Vitamin $D_2$ concentration in the pellet was found to be 77.26 µg mL$^{-1}$ compared to only 1.4 µg mL$^{-1}$ in the supernatant. Therefore, vitamin concentration in the nanoparticle pellet was 55 times higher than vitamin concentration in the serum, and 5.7 times higher than the initial concentration of the vitamin in the dispersion (13.5 µg mL$^{-1}$).

Example 4

Protective Effect of β-Lactoglobulin-Pectin Complexes on Vitamin D2 Stability

Figure 7:
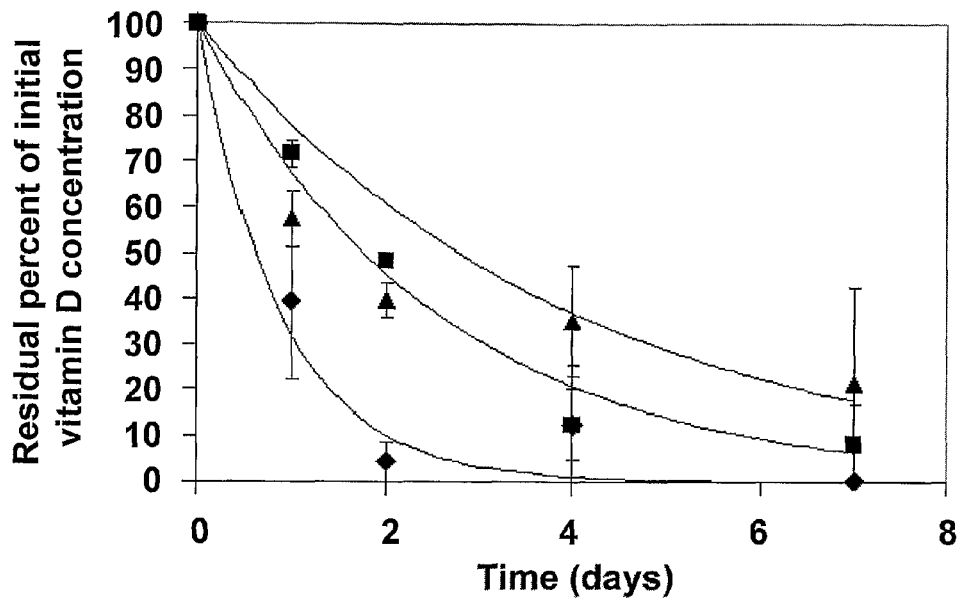
FIG. 7: Effect of encapsulation on stability of vitamin D during an accelerated shelf-life stress test at pH 4.25: samples were stored at 30° C. in closed vials containing 10 mL of solution and 10 mL of air, for a period of 125 hours: (■) $VD_2$-loaded β-lactoglobulin) (▲) complexes of $VD_2$-β-lactoglobulin-pectin (pH 4.25). (♦) control of unprotected $VD_2$ in water.

FIG. 7 shows the protective effect of β-lactoglobulin-pectin complexes on bound vitamin $D_2$ compared to β-lactoglobulin-only, and to an unprotected control (vitamin D dispersion in water), during an accelerated shelf-life stress test at pH 4.25: samples were stored at 30° C. in closed vials containing 10 mL of solution and 10 mL of air, for a period of 125 hours. Degradation under these conditions is apparently caused by oxygen and light. The results show the slowest degradation of the vitamin in the β-lactoglobulin-pectin nanocomplexes followed by the vitamin entrapped in β-lactoglobulin only. The fastest degradation rate was observed in the unprotected control.

Example 5

β-Lactoglobulin-Chitosan Electrostatic Complex Formation

A series of solutions containing a constant protein concentration (0.05% wt) and varying chitosan concentrations (0-0.95% wt) was prepared by adding different amounts of 0.2% wt stock chitosan solutions and double distilled water (ddw) or buffer to 5 ml 0.2% wt β-lactoglobulin stock protein solution. The 120 kDa, 84.5% deacetylated chitosan, is only soluble in acid environment, therefore we dissolved it in 5 mM acetic acid solution and titrated it to pH 3 with HCl in order to achieve full dissolution. 15 kDa chitosan, 85% deacetylated, was dissolved either in filtered ddw or in 5 mM acetic acid. β-lactoglobulin and chitosan were dissolved for at least 6 hours and then mixed together in different ratios. Mixing the protein and the chitosan was carried out in two different ways: (1) Titled: "pH 3-6 method": the protein was mixed with the chitosan at pH 3, and the solution was brought up to volume with 5 mM acetic acid, and then the solution was titrated to the final pH 6 while stirring; (2) Titled: "pH near 6 method": The 120 kDa chitosan solution dissolved in acetic acid was brought to pH 6 and then stirred into the protein solution; the 15 kDa chitosan solution dissolved in ddw was mixed with the protein under continues stirring. In either case, the solution was brought up to volume with ddw after mixing with the protein and the pH was slightly corrected to a final pH of 6 by HCl or NaOH. Solutions were then stirred for 1 hour and stored overnight at room temperature prior to analysis.

Transparent solutions were obtained in the majority of the samples particularly above 0.075% chitosan (FIG. 8). Zeta potential measurements showed fair colloidal stability of the β-lactoglobulin-chitosan complexes (FIG. 9).

Example 6

The Effect of Chitosan Concentration on Particle Size of β-Lactoglobulin-Chitosan Complexes Particle size of β-lactoglobulin-chitosan complexes was influence by the method of mixing β-lactoglobulin with chitosan and by chitosan concentration (FIG. 10). Consider particle size in complexes using the 120 kDa chitosan: when mixing the protein with the chitosan at a pH far below the complexation pH and then titrating slowly to the optimal interaction pH, particles obtained were smaller than those obtained by forming the complexes while mixing at pH 6. When the chitosan and the protein were at pH 3, they were both positively charged and therefore repelled each other, giving a homogeneous solution. While increasing the pH, complexes were formed slowly, resulting in small particles. When forming similar complexes with the 120 kDa chitosan in the "pH near 6 method", where the protein and chitosan are near the pH of maximal interaction during mixing, big aggregates quickly appeared, probably due to a fast spontaneous aggregation due to strong attraction. The high molecular weight of this chitosan apparently resulted in large metastable complexes. Complexes formed using the 15 kDa chitosan, on the other hand, were less influenced by the mixing method, as particles were smaller in the "pH near 6 method". Therefore, in instances using 15 kDa chitosan, the ionic strength was probably more significant than for the 120 kDa based particles. Adjusting the pH from 3 to 6 in 15 kDa containing solutions resulted in increasing the ionic strength and creating particles with less repulsion between them. Consequently bigger aggregates were formed.

Example 7

Encapsulation of Vitamin D2 in β-Lactoglobulin-Chitosan Complexes and Effect on Particle Size Parameters selected for β-lactoglobulin-chitosan complex formation were those demonstrated in Example 6 to produce stable dispersions of β-lactoglobulin-chitosan nanoparticles. The conditions and process used were: 0.05% wt β-lactoglobulin, 0.15% wt chitosan 15 kDa and employing the "pH near 6 method". The resulting colloidal dispersion had a zeta potential of ~23 mV, a small particle size (~176 nm) and was quite transparent.

Incorporation of vitamin D2, as an exemplary fat-soluble vitamin, into β-lactoglobulin-chitosan complexes necessitated binding the vitamin D2 to β-lactoglobulin prior to chitosan addition. Vitamin $D_2$ dissolved in 100% ethanol (5 mg/ml) was added to β-lactoglobulin solution at pH≈6.9 and stirred for half an hour. Chitosan was added to the solution at three of the chitosan concentrations that gave the best results, as previously determined in Example 6 (0.125%, 0.15%, and 0.2%), then the pH was adjusted to 6.00±0.02, and the solution was stirred for another hour. The results of turbidity measurements and particle size are presented in Table 3 below. β-lactoglobulin-chitosan nanoparticles formed at all three chitosan concentrations were relatively clear, though not completely transparent. Particle size increased slightly compared to β-lactoglobulin chitosan complex particles without the vitamin.

TABLE 3

Turbidity and particle size of β-lactoglobulin - chitosan-vitamin D2 complexes

| particle size (nm) | turbidity (600 nm) | chitosan concentration (% wt) |
|---|---|---|
| 194 ± 7 | 0.036 | 0.125 |
| 203 ± 6 | 0.038 | 0.150 |
| 209 ± 1 | 0.033 | 0.200 |

Example 8

Binding Omega-3 Polyunsaturated Fatty Acid, DHA, to β-Lactoglobulin

A spectrofluorometry method was used to study the binding of DHA to β-lactoglobulin. Measurements were made of the binding-induced quenching of the intrinsic fluorescence of tryptophanyl residue TRP19 found in the hydrophobic β-barrel of β-lactoglobulin, using excitation and emission wavelengths of 287 and 332 nm respectively. A volume of 2.5 ml of 1 µM β-lactoglobulin solution in 100 mM Tris-HCl buffer solution (pH 7.0) was titrated with 11 incremental aliquots ranging from 2 to 10 µL of 0.2 µM DHA dissolved in ethanol. Measurements were performed in duplicate. The apparent dissociation constant and the number of DHA molecules involved in binding per β-lactoglobulin molecule were calculated from plots of the fluorescence intensity, expressed as the percentage of the initial fluorescence of DHA-free β-lactoglobulin vs. added DHA concentration. All measurements were performed at 25° C.

Figure 11:
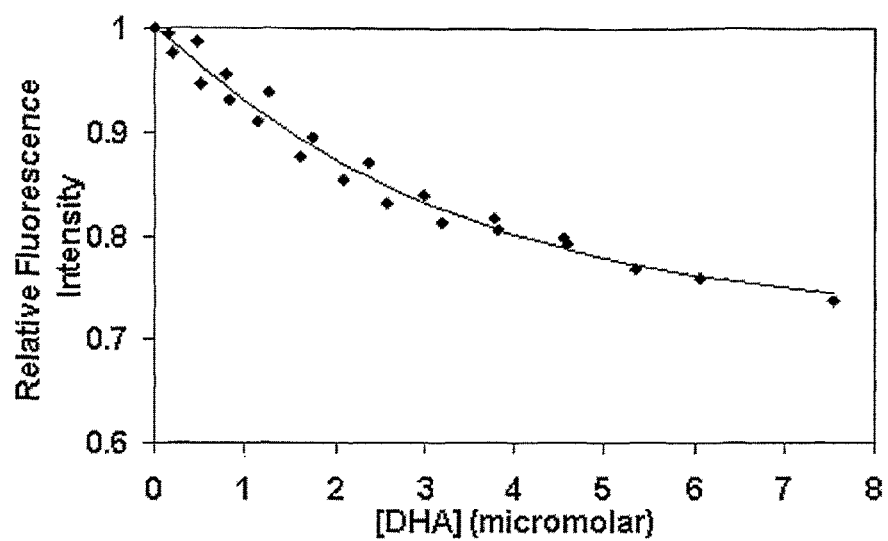
FIG. 11: Spectroscopic analysis of the binding of docosahexaenoic acid (DHA) to β-lactoglobulin at pH 7.0 (100 mM Tris-HCl buffer) and 25° C. The symbols represent experimental points of duplicate titration runs, while the solid line represents high affinity associations model fit (Christiaens et al., 2002, *Eur. J. Biochem,* 269:2918). The analysis suggested that 2.67±1.26 moles of DHA were bound per mole of β-lactoglobulin, with $K_b=(6.75\pm1.38)*10^5 M^{-1}$.

The tryptophan-fluorescence quenching results, showed spontaneous binding of DHA to β-lactoglobulin, (FIG. 11).

The spectrofluorometry raw data raw was analyzed using Matlab™ (The MathWorks, Inc.), according to the model described by Christiaens et al. 2002, *Eur. J. Biochem.* 269: 2918-26. According to this analysis, 2.7 moles of DHA were bound per one mole of β-lactoglobulin, with a binding constant of $K_b=7.02E+05$ M$^{-1}$. Without wishing to be bound by theory or mechanism of action, it should be kept in mind that because only the central binding site in the β-barrel is "reporting" by its internal tryptophanyl residue, the resulting stoichiometry reflects binding to this site, as well as to any other site of equal or higher affinity to DHA which would be saturated with or before the central binding site. Without wishing to be bound by any theory or mechanism of action, because the pI of lactoglobulin is 5.18, and the pKa of DHA is ≈8.5 (Namani et al., 2007, *Colloids and Surfaces, B: Biointerfaces*, 54: 118-123) these compounds are electrostatically repelling each other at pH 7, as they are both negatively charged. Thus, at neutral pH, their binding is most likely based on hydrophobic interactions. At acidic pH the binding interaction of β-lactoglobulin and DHA is increased, as DHA becomes almost completely uncharged, and β-lactoglobulin becomes positively charged.

Example 9

Encapsulation of DHA in β-Lactoglobulin-Pectin Complexes and Effect on Particle Size Incorporation of DHA, as an exemplary omega-3 polyunsaturated fatty acid, into β-lactoglobulin-pectin complexes necessitated binding DHA to β-lactoglobulin prior to pectin addition. To assess the effect of protein concentration on the nanocomplexes, solutions were prepared at two final β-lactoglobulin concentrations of 0.05% and 0.2% wt, a β-lactoglobulin:DHA molar ratio of 1:2 and a varying final concentration of pectin. Complexes were titrated to pH 4.5.

Figure 12:
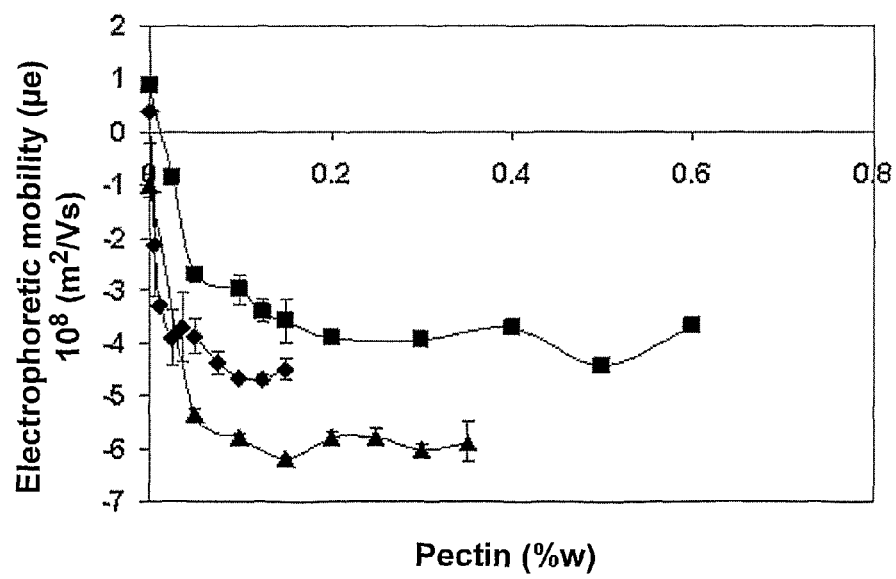
FIG. 12: Electrophoretic mobility of DHA-loaded β-lactoglobulin-pectin complexes (molar ration 1:2 β-lactoglobulin: DHL), at pH 4.5 (low ionic strength) and 25° C., as a function of pectin concentration: (▲) 0% β-lactoglobulin; (♦) 0.05% β-lactoglobulin; (■) 0.2% β-lactoglobulin.
Figure 13:
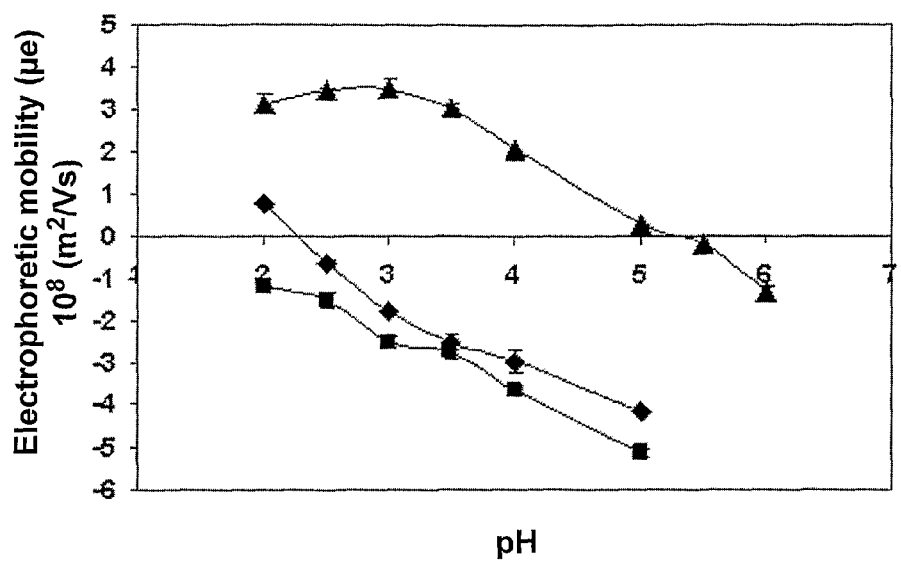
FIG. 13: Electrophoretic mobility versus pH, of: (▲) 0.05% β-lactoglobulin; (♦) a system containing 0.05% β-lactoglobulin, 0.22 mM DHA (molar ratio of 1:2 β-lactoglobulin:DHA), and 0.05% pectin; and (■) 0.05% pectin, all of them at 25° C. and low ionic strength.
Figure 14:
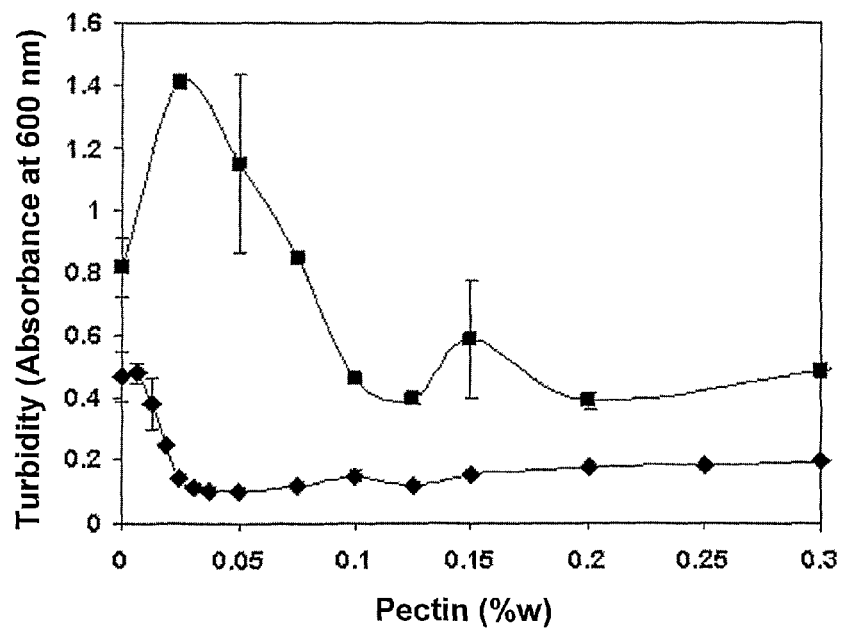
FIG. 14: Turbidity (absorbance at 600 nm) of concentrated complex dispersions containing 0.2% β-lactoglobulin (■), and the diluted dispersions containing 0.05% β-lactoglobulin (♦) at pH 4.5 (low ionic strength), 25° C. and final DHA concentrations at a molar ratio of 1:2 (β-lactoglobulin:DHA).
Figure 15:
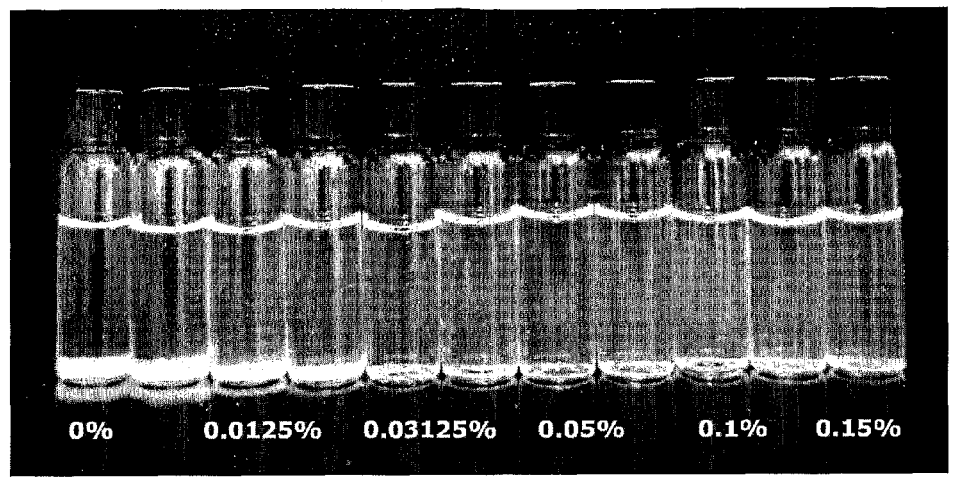
FIG. 15: Vials containing a series of 0.05% w β-lactoglobulin solutions, at pH 4.5 (low ionic strength—no salt or buffer added) and 25° C., with DHA at a molar ratio of 1:2 (β-lactoglobulin:DHA) at increasing pectin concentrations.
Figure 16:
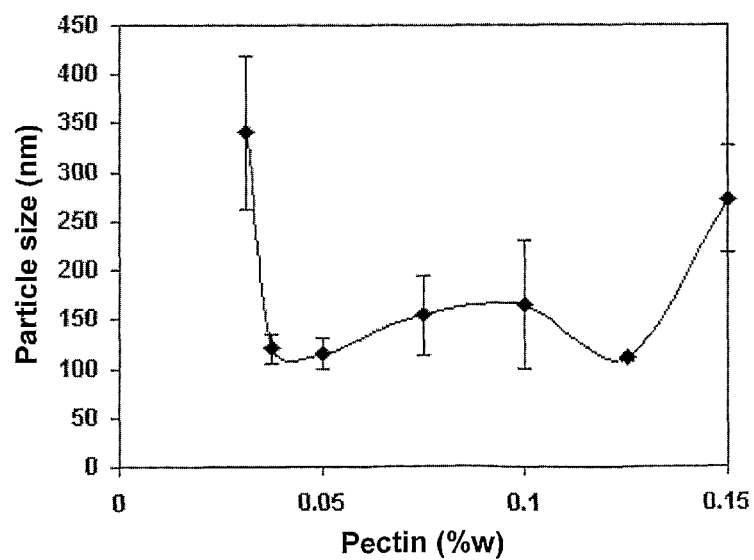
FIG. 16: Mean (Gaussian) diameter of complexes made with 0.05% β-lactoglobulin and DHA (molar ratio 1:2) and increasing pectin concentrations, at pH 4.5 (low ionic strength) and 25° C.

The stability of these colloidal systems was studied by measuring the electrophoretic mobility (EM) of the colloidal particles (FIGS. 12 and 13). Because the ionic strength of the studied systems was very low, and the particles are both very small and "soft" (being aggregates of oppositely charged polymers), the precise calculation of zeta potential from EM is not possible, due to the complexity of the system, and the limitations of currently available theoretical models. Still, we used the Smoluchowski model, which gives the lowest zeta potential estimate for a given EM value, among the commonly used models (Delgado et al., 2005, *Pure Appl. Chem.*, 77:1753-1805), as a conservative lower limit. Particles having a sufficiently high electrostatic repulsion resist flocculation and their colloidal system would be stable. Suspensions with zeta potential values more negative than −40 mV generally have good colloidal stability (ASTM, 1985, 4187-82). As the pectin concentration was increased, the EM and hence the zeta potential of both the more concentrated and the diluted systems decreased, reaching a plateau above 0.1% pectin and 0.2% pectin, for the 0.05% and 0.2% protein systems, respectively (FIG. 12). Using the Smoluchowski model as an underestimation, the plateau EM values suggest that zeta potential values are more negative than −60 and −50 mV, respectively, suggesting a very good colloidal stability Already above 0.05 and 0.0125 wt % pectin, respectively, complexes presented an EM lower than about −3×10$^8$ m$^2$/Vs, i.e. zeta potential lower than −40 mV, an indication of good colloidal stability of the system both before and after dilution. It should also be noted that at pH 4.5, the DHA-loaded β-lactoglobulin particles were unstable, as evident from both the low positive EM, (FIG. 12), and the visible precipitation (FIG. 15). This observation suggests that at this pH the addition of pectin is essential for the colloidal stability of β-lactoglobulin:DHA complexes, which is in accordance with observations that anionic polysaccharides that form complexes with proteins can inhibit aggregation and precipitation of protein particles near the protein pI, as the complex pI is shifted to lower pH values (Tolstoguzov, 1997, *Food Prot. and their Appl.* 171-98, CRC Press). The dependence of EM of these nanocomplexes on pH was studied, as depicted in FIG. 13. Here, β-lactoglobulin concentration was at 0.05%, DHA at 0.22 mM (1:2 molar ratio of β-lactoglobulin:DHA), and pectin at 0.05 wt %. It can be seen that the isoelectric point of the complexes under these conditions was 2.26. The figure also shows the EM of pure β-lactoglobulin solutions, and of pure pectin solutions for comparison. The isoelectric point of β-lactoglobulin based on this graph was 5.2, in good agreement with the literature. A central aim of the invention is to form small enough nanoparticles which would allow enrichment of clear acid beverages. FIG. 14 shows the turbidity results of both the 0.2% β-lactoglobulin ('concentrated' or 'stock β-lactoglobulin solution') systems, and the diluted, 0.05% β-lactoglobulin, systems. The higher concentration systems showed quite a high turbidity, however, after dilution to 0.05% β-lactoglobulin, clear dispersions were obtained, as can be seen in FIG. 14. When only protein was present (with or without the bound ligand) below its isoelectric point, it was expectedly positively charged, as evident from the positive EM (FIG. 12,13). As pectin concentration was increased (FIG. 14), sub-micron pectin-protein complexes started forming, with pectin gradually neutralizing the positive charge of the protein. This lead to increasing turbidity, reaching a maximum value at 0.00625 and 0.025 wt % (for 0.05 and 0.2 wt % β-lactoglobulin, respectively), concentrations at which the zeta potential was closest to zero, as reflected by the EM (FIG. 12). This resulted in complex coacervation and precipitation, as can be seen in FIG. 15. Further increase of the pectin concentration caused a decrease in turbidity until minima were observed, corresponding to 0.0375 and 0.125 wt % pectin (for 0.05 and 0.2 wt % β-lactoglobulin, respectively). This clarification of the system was due to rising negative charge caused by increasing the excess of pectin in the particles. Consequently, larger electrostatic and steric repulsion resulted in less aggregation and formation of smaller particles (FIG. 16). Lastly, further increase of the pectin concentration caused a slight increase in the turbidity of the solutions, possibly indicating approaching the solubility limit of these complexes under the given conditions. According to FIG. 16, the minimal mean diameter was about 110 nm, and it corresponded to a pectin concentration between 0.0375 and 0.125 wt %. As the apparent increase in particle size at higher pectin concentrations is more significant than the increase in turbidity, we hypothesized without wishing to be bound by theory or mechanism of action that the increase in pectin concentration increased the viscosity, causing decreased particle mobility, interpreted by the DLS as increased particle size. To test this hypothesis, we added a 240 nm polystyrene latex particle-size standard to samples identical to those shown in FIG. 17 at pectin concentrations of 0.0375 and 0.15%, and determined the size distribution with the PSS Nicomp™ 380 DLS, using the Nicomp algorithm. The size obtained for the 240 nm standard peak increased to 270±8 and 354±8 nm for 0.0375 and 0.15% pectin (both with 0.05% β-lactoglobulin, and DHA), respectively, i.e. the microviscosity increased 1.3-fold—the ratio of the apparent sizes obtained for the standard (354/270) when pectin concentration was raised from 0.0375 to 0.15%, explaining most of the apparent size increase from 110 to 272 nm observed in FIG. 16. The rest of the increase, as well as the larger standard error, may be explained by the presumed irregular "hairy" shape of the nanocomplexes which are probably more affected by the added pectin compared to the smooth latex standard beads. Taking into account the microviscosity correction factor obtained by the ratio of the standard size in water and in the 0.0375% pectin system (240/270), the minimal particle size (of 110 nm) was somewhat overestimated, and it was in fact about 100 nm.

Example 10

Analysis of the DHA Encapsulation Efficiency

The overall DHA extraction and analysis yield (including pellet and supernatant) was 100.6±7.1% (average±standard error) of the total initially added amount, indicating that the DHA extraction method and the RP-HPLC analysis were suitable for the determination of DHA in the studied system. The encapsulation efficiency, i.e. the amount of DHA in the pellet as percent of the initially added DHA amount, was 64±10%. The DHA concentration in the pellet was on average 166±23 times higher than the concentration found in the supernatant. This fact suggests that DHA has a much higher affinity for the β-lactoglobulin-pectin complexes compared to the surrounding serum. This result also corroborates the results of the binding of DHA to β-lactoglobulin, and confirms that good affinity remains even after pH is decreased to 4.5 (it may in fact be even improved, as the hydrophobicity of DHA increases and its electrostatic repulsion from β-lactoglobulin vanishes as the ionization of the fatty acid decreases with pH).

Example 11

Figure 17:
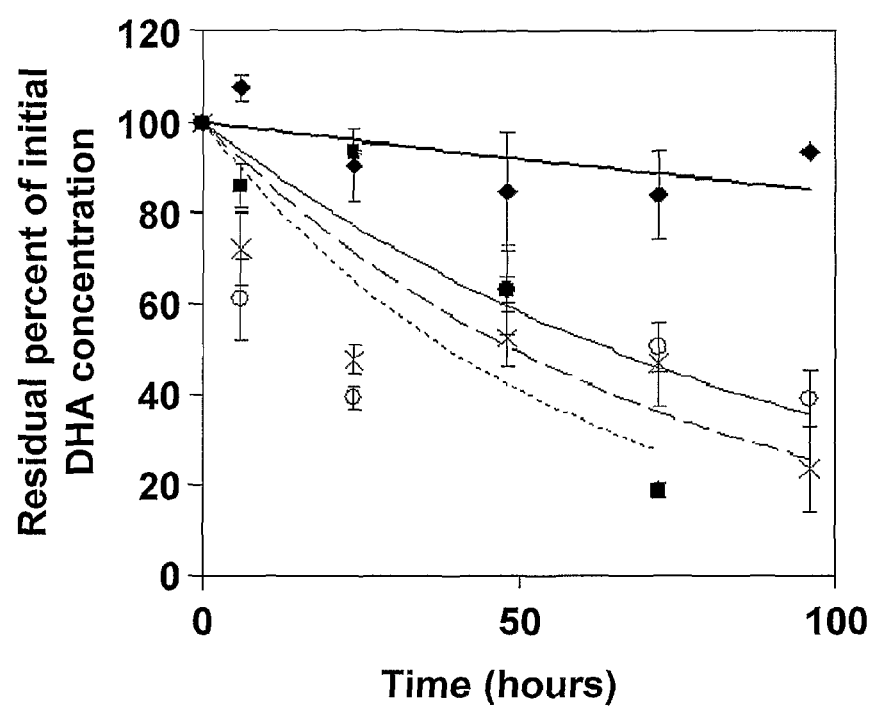
FIG. 17: DHA stability during a stress test at 40° C. and low ionic strength: (■, ------) DHA in water (pH 4.5); (x, - - -) DHA in water (pH 7.0); (o, —) β-lactoglobulin+DHA at pH 7.0; (▲, __ )β-lactoglobulin+DHA+pectin at pH 4.5. Exponential lines are drawn to guide the eye, and are not intended to provide a rigorous kinetic analysis.

Protective Effect of β-Lactoglobulin-Pectin Complexes on DHA Against Degradation To study the oxidation stability conferred by the different β-lactoglobulin and pectin systems to the encapsulated DHA we used an accelerated shelf-life stress test at 40° C. The results were fitted with exponential trendlines, as a first-order approximation of the DHA degradation kinetics. As shown in FIG. 17, the various samples tested may be ranked in order of increasing protective effect as follows: DHA in water (pH 4.5)<DHA in water (pH 7.0)<β-lactoglobulin+DHA at pH 7.0<β-lactoglobulin+DHA+pectin at pH 4.5. The partial protection by β-lactoglobulin may be explained by its mild antioxidant activity, apparently due to its free thiol. However, the complex comprising both β-lactoglobulin and pectin conferred the highest protection against oxidation to DHA, resulting in only about 5-10% loss during 100 hours, compared to about 80% loss when the unprotected DHA was monitored. This suggests that the formation of the β-lactoglobulin-DHA/pectin complexes are effective in retarding DHA degradation. Without wishing to be bound by theory or mechanism of action this may be due to the fact that DHA is immobilized by the protein and shielded by the protein-pectin complex and hence its reactivity is reduced, and so is the accessibility of oxidizing agents to DHA.

The invention claimed is:
1. A stable colloidal dispersion of nanoparticles comprising an isolated β-lactoglobulin, a polysaccharide and at least one bioactive compound selected from the group consisting of a vitamin, a nutraceutical and a pharmaceutical, wherein the bioactive compound is bound to the β-lactoglobulin, wherein the amount of polysaccharide in the dispersion of nanoparticles is equal to or higher than the amount of β-lactoglobulin, and wherein said dispersion of nanoparticles has an absorbance of less than 0.25 at 600 nm in an aqueous medium, said dispersion being transparent in an aqueous medium.
2. The dispersion of nanoparticles according to claim 1, wherein said dispersion of nanoparticles has an absorbance of less than 0.1 at 600 nm in an aqueous medium.
3. The dispersion of nanoparticles according to claim 1, wherein the nanoparticles do not comprise cross-linking agents.
4. The dispersion of nanoparticles according to claim 1, wherein the weight ratio between the β-lactoglobulin and the polysaccharide is between 1:1 and 1:5.
5. The dispersion of nanoparticles according to claim 1 comprising up to 0.5 wt % of β-lactoglobulin.
6. The dispersion of nanoparticles according to claim 1 comprising 0.05 wt % of β-lactoglobulin.
7. The dispersion of nanoparticles according to claim 1, wherein the mean diameter of the nanoparticles is between 20 and 400 nm.
8. The dispersion of nanoparticles according to claim 7, wherein the mean diameter of said nanoparticles is between 40 and 150 nm.
9. The dispersion of nanoparticles according to claims 1, wherein the polysaccharide is selected from the group consisting of pectin, alginic acid, xanthan gum, hyaluronic acid, chondroitin sulfate, gum arabic, gum karaya, gum tragacanth, carrageenan, agaropectin and chitosan.

10. The dispersion of nanoparticles of claim 1, wherein the polysaccharide is an anionic polysaccharide.

11. The dispersion of nanoparticles according to claim 10, wherein the anionic polysaccharide is pectin.

12. The dispersion of nanoparticles according to claims 10, wherein the dispersion of nanoparticles is present in an aqueous solution having a pH below the pI of β-lactoglobulin.

13. The dispersion of nanoparticles according to claim 12, wherein the aqueous solution has a pH between 3.0 and 5.0.

14. The dispersion of nanoparticles of claim 1, wherein the bioactive compound is hydrophobic.

15. The dispersion of nanoparticles of claim 1 comprising β-lactoglobulin and bioactive compound in a molar ratio of 3:1 to 1:10.

16. The dispersion of nanoparticles according to claim 1, wherein the vitamin is selected from the group consisting of vitamin D, vitamin E, vitamin A and vitamin K and the nutraceutical is selected from the group consisting of an essential fatty acid, a phytoestrogen and an antioxidant.

17. The dispersion of nanoparticles according to claim 1, wherein the bioactive compound is selected from the group consisting of an omega-3 fatty acid and conjugated linoleic acid.

18. The dispersion of nanoparticles according to claim 17, wherein the polysaccharide is pectin.

19. The dispersion of nanoparticles according to claim 1, wherein less than 20% of the bioactive compound is degraded or oxidized within 100 hours at 40° C.

20. A food composition or beverage comprising a dispersion of nanoparticles according to claim 1 and a low-fat or non-fat food or beverage.

21. A pharmaceutical composition comprising a dispersion of nanoparticles according to claim 1.

22. A composition comprising dehydrated nanoparticles according to claim 1.

23. A stable colloidal dispersion of nanoparticles comprising an isolated β-lactoglobulin and a polysaccharide, wherein the amount of polysaccharide in the dispersion of nanoparticles is equal to or higher than the amount of β-lactoglobulin and wherein the dispersion of nanoparticles has an absorbance of less than 0.1 at 600 nm in an aqueous medium, said dispersion being transparent in an aqueous medium.

24. The dispersion of nanoparticles according to claim 23, wherein the nanoparticles do not comprise cross-linking agents.

25. The stable colloidal dispersion of nanoparticles according to claim 23, wherein the polysaccharide is an anionic polysaccharide and wherein the dispersion of nanoparticles is present in an aqueous solution having a pH below the pI of β-lactoglobulin.

26. The stable colloidal dispersion of nanoparticles according to claim 23, wherein the polysaccharide is a cationic polysaccharide and wherein the dispersion of nanoparticles is present in an aqueous solution having a pH above the pI of β-lactoglobulin.

27. The dispersion of nanoparticles according to claim 1, comprising an excess of polysaccharide relative to the β-lactoglobulin, wherein the β-lactoglobulin is located in the inner part of the nanoparticles, which is coated by the polysaccharide.

28. A food composition or beverage comprising
a stable colloidal dispersion of nanoparticles comprising an isolated β-lactoglobulin, a polysaccharide and at least one bioactive compound selected from the group consisting of a vitamin, a nutraceutical and a pharmaceutical, wherein the bioactive compound is bound to the β-lactoglobulin, and wherein the amount of polysaccharide in the dispersion of nanoparticles is equal to or higher than the amount of β-lactoglobulin; and
a low-fat or non-fat food or beverage.

* * * * *